(12) United States Patent
Stoddart et al.

(10) Patent No.: US 9,546,169 B2
(45) Date of Patent: Jan. 17, 2017

(54) REDOX ACTIVE TRIANGULAR ORGANIC MATERIALS

(71) Applicants: NORTHWESTERN UNIVERSITY, Evanston, IL (US); KING ABDULAZIZ CITY FOR SCIENCE AND TECHNOLOGY (KACST), Riyadh (SA)

(72) Inventors: James Fraser Stoddart, Evanston, IL (US); Severin T. Schneebeli, Burlington, VT (US); Zhichang Liu, Evanston, IL (US); Marco Frasconi, Narni (IT)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/845,205

(22) Filed: Sep. 3, 2015

(65) Prior Publication Data
US 2016/0130271 A1    May 12, 2016

Related U.S. Application Data

(60) Provisional application No. 62/045,531, filed on Sep. 3, 2014.

(51) Int. Cl.
C07D 471/08 (2006.01)
H01L 51/00 (2006.01)
C07D 471/06 (2006.01)

(52) U.S. Cl.
CPC .................................. *C07D 471/06* (2013.01)

(58) Field of Classification Search
USPC ............................................ 546/66; 313/505
See application file for complete search history.

(56) References Cited

PUBLICATIONS

Kaik, M. et al.: Unprecedented selectivity in the formation of large-ring oligoimines from conformationally bistable chiral diamines. Organic Letters, vol. 8, pp. 2921-2924, 2006.*
Schneebeli ST, et al., "Electron Sharing and Anion—πRecognition in Molecular Triangular Prisms," Angew. Chem. Int. Ed. Engl. 52:13100-4 (2013).
Liu Z, et al., "Assembly of supramolecular nanotubes from molecular triangles and 1,2-dihalohydrocarbons," J. Am. Chem. Soc. 136:16651-60 (2014).

* cited by examiner

*Primary Examiner* — Charanjit Aulakh
(74) *Attorney, Agent, or Firm* — Klintworth & Rozenblat IP LLC

(57) ABSTRACT

A redox-active triangular prism is provided. The redox-active triangular prism includes a plurality of pure enantiomers selected from a group consisting of (−)-NDI-Δ and (+)-NDI-Δ. Methods for their preparation as solvent-templated supramolecular structures and a characterization of their redox-active behavior are provided.

22 Claims, 18 Drawing Sheets

REDOX ACTIVE TRIANGULAR ORGANIC MATERIALS

CROSS-REFERENCE TO RELATED APPLICATIONS

This application claims benefit of priority under 35 U.S.C. 119 to U.S. provisional patent application Ser. No. 62/045,531, filed Sep. 3, 2014, and entitled "REDOX ACTIVE TRIANGULAR ORGANIC MATERIALS," the contents of which are herein incorporated by reference in its entirety.

BACKGROUND

1. Technical Field

The present disclosure relates to composition and methods for preparing rigid triangular molecular prisms containing redox-active centers and template-specific structures including the same for use in molecular electronics.

2. Description of Related Art

Electronic interactions, as well as through-space electron hopping and delocalization between redox-active aromatic building blocks, play a crucial role in orchestrating electron transport in organic materials. Extensive investigations of orbital overlap associated with both parallel and T-shaped geometries between aromatic rings contribute to design of efficient organic photovoltaics and molecular electronic devices. Little is know about whether through-space orbital overlap and electron sharing in non-traditional (that is, non-parallel) geometries between multiple rings affect the properties of aromatic compounds and their superstructures. Furthermore, practical principles do not exist for preparing template-specific structures that include such compounds.

BRIEF SUMMARY

In a first aspect, a redox-active triangular prism is provided. The redox-active triangular prism includes a plurality of pure enantiomers selected from a group consisting of (−)-NDI-Δ and (+)-NDI-Δ.

In a second aspect, a method of making a redox-active triangular prism is provided. The method includes several steps. The first step includes preparing a mixture that includes naphthalene-tetracarboxylic dianhydride, a pure enantiomer selected from a group consisting of (RR)-trans-1,2-cyclohexanediamine ((RR)-2) and (SS)-trans-1,2-cyclohexanediamine ((SS)-2) and a solvent. The second step includes incubating the mixture at a temperature above ambient temperature.

In a third aspect, an electrode comprising a redox-active triangular prism is provided. The redox-active triangular prism includes a plurality of pure enantiomers selected from a group consisting of (−)-NDI-Δ and (+)-NDI-Δ, or a solvent-crystalline complex thereof.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The features, objects and advantages other than those set forth above will become more readily apparent when consideration is given to the detailed description below. Such detailed description makes reference to the following drawings.

In FIGS. 8A and 8B, the four nonequivalent NDI-Δ units are highlighted in purple, orange, blue, and red, respectively. Green arrows indicate the net rotation angles between the NDI-Δ units a and a' as well as b and b'. Double-colored arrows show the relative rotation angle between the neighboring NDI-Δ units. Hydrogen bonds are depicted as magenta hatched lines.

Figure 1A:
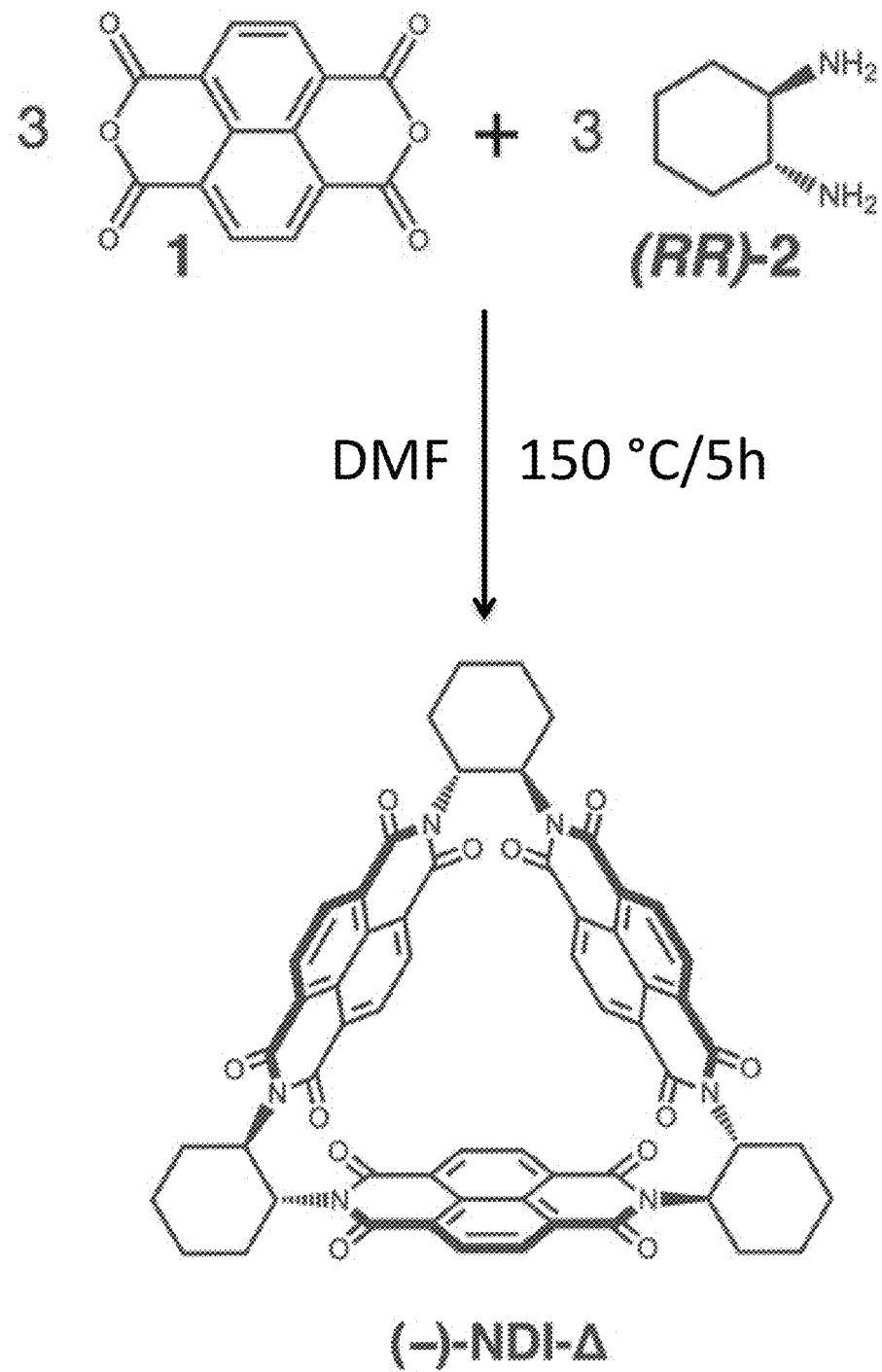
FIG. 1A depicts an exemplary stereospecific synthesis of the rigid triangular molecular prism (−)-NDI-Δ from (RR)-2. The enantiomer (+)-NDI-Δ was prepared in a similar yield from (SS)-2 following the same procedure as that used to prepare the (−)-enantiomer.

While the present invention is amenable to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments and claims herein for interpreting the scope of the invention.

DETAILED DESCRIPTION

The compositions and methods now will be described more fully hereinafter with reference to the accompanying drawings, in which some, but not all permutations and variations of embodiments of the invention are shown. Indeed, the invention may be embodied in many different forms and should not be construed as limited to the embodiments set forth herein. These embodiments are provided in sufficient written detail to describe and enable one skilled in the art to make and use the invention, along with disclosure of the best mode for practicing the invention, as defined by the claims and equivalents thereof.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, enantiomeric triangular naphthalenediimide-based macrocycles (RRRRRR)- and (SSSSSS)-NDI-Δ, are designated as (−)-NDI-Δ and (+)-NDI-Δ, respectively. Similarly, the terms (−)-NDI-Δ and (+)-NDI-Δ are referred to as R-Δ and S-Δ, respectively. Thus, recital of enantiomeric triangular naphthalenediimide-based macrocycle (RRRRRR)-NDI-Δ, (−)-NDI-Δ and R-Δ have the same meaning and are used interchangeably herein. Likewise, recital of enantiomeric triangular naphthalenediimide-based macrocycle (SSSSSS)-NDI-Δ, (+)-NDI-Δ and S-Δ have the same meaning and are used interchangeably herein.

Overview

Applicants designed and synthesized rigid chiral triangular prisms composed of enantiomeric triangular naphthalenediimide-based macrocycles (RRRRRR)- and (SSSSSS)-NDI-Δ, which are designated as (−)- and (+)-NDI-Δ, respectively, that are tubular cavities flanked by three naphthalenediimide (NDI) units. NDI is an ideal building block to explore electron-transport and delocalization owing to its unique redox properties and accessible functionalization. Furthermore, the highly electron-deficient nature of NDIs is of current interest for the investigation of anion-π interactions with potential applications in chemo-sensing, synthetic membrane transport and selective catalysis. The cyclic through-space electron sharing takes place in the NDI-molecular prisms as a consequence of the unique triangular arrangement of their NDI units. Rigid triangular geometries are special in so far as they: 1) allow for efficient orbital overlap on account of the 60° contact angles involved and 2) contain, at the same time, cavities capable of expressing molecular recognition. Moreover, the cyclic orbital overlap in the NDI-based molecular triangular prisms (−)- and (+)-NDI-Δ leads to 3) electronic communication between the NDI units, resulting in no less than six individually accessible redox states; 4) enhanced anion-π recognition with bound linear $I_3^-$ anions; and 5) $I_3^-$ induced π-π stacking into single-handed helical superstructures that are 6) right-handed (P) and left-handed (M), respectively, as a result of chirality transfer from the molecule to the supramolecule. Finally, a class of similar solvents including the 1,2-dihalo-ethanes and 1,2-dihalo-ethenes (DXEs) drives highly specific assembly of a diverse range of supramolecular nanotubes from the enantiomeric triangular naphthalenediimide-based macrocycles (−)- and (+)-NDI-Δ.

Compositions and Methods of Synthesis

Figure 1B:
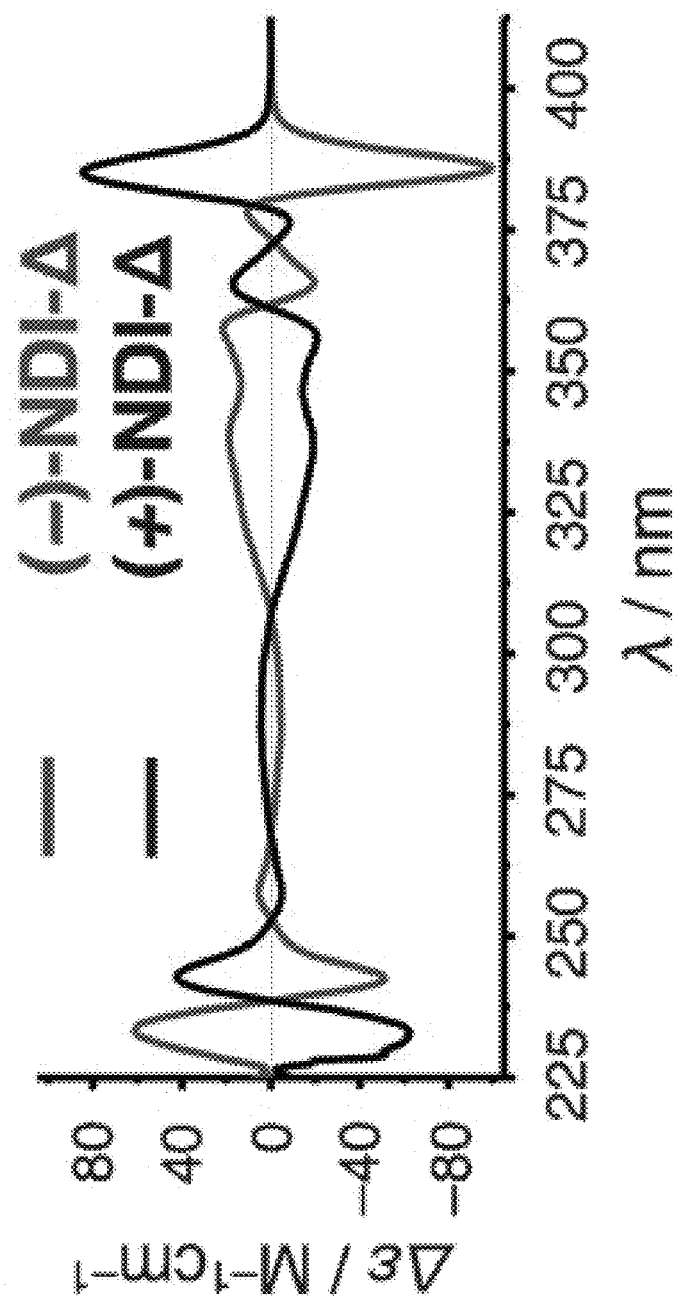
FIG. 1B depicts exemplary CD spectra of (−)- and (+)-NDI-Δ recorded at 298 K in $CH_2Cl_2$ solutions.
Figure 1C:
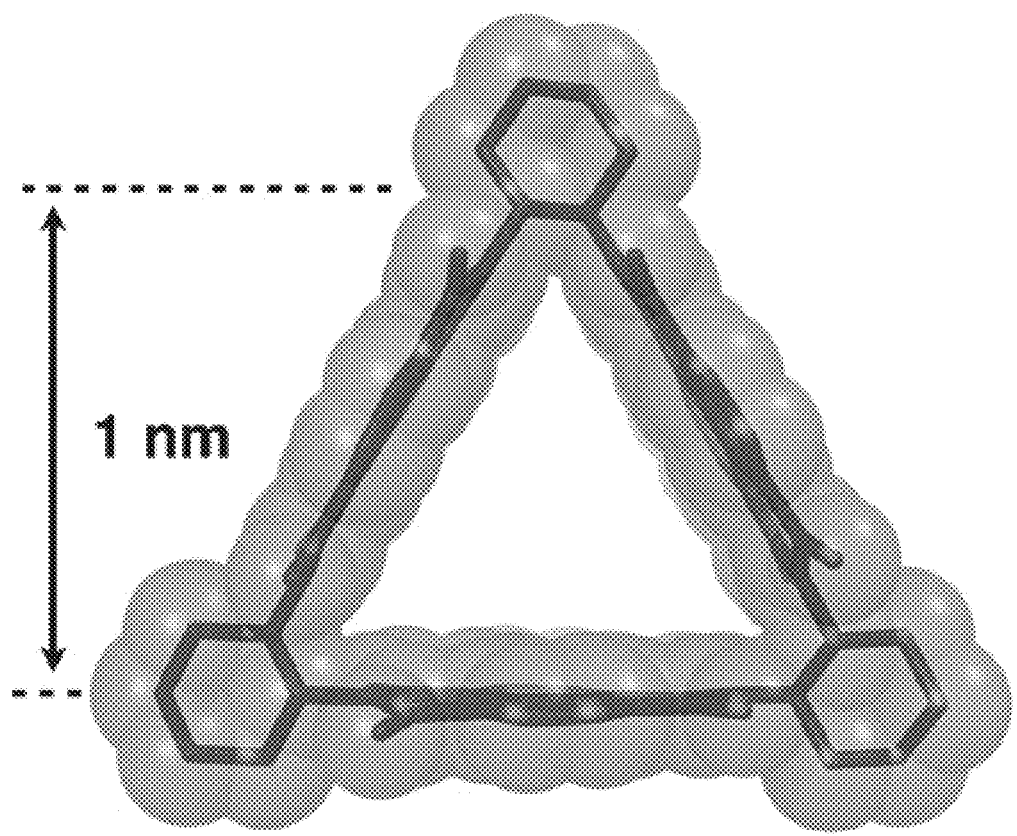
FIG. 1C depicts a tubular representation of the single-crystal X-ray structure of (−)-NDI-Δ with the corresponding space-filling representation superimposed upon it in a semi-transparent fashion.
Figure 1D:
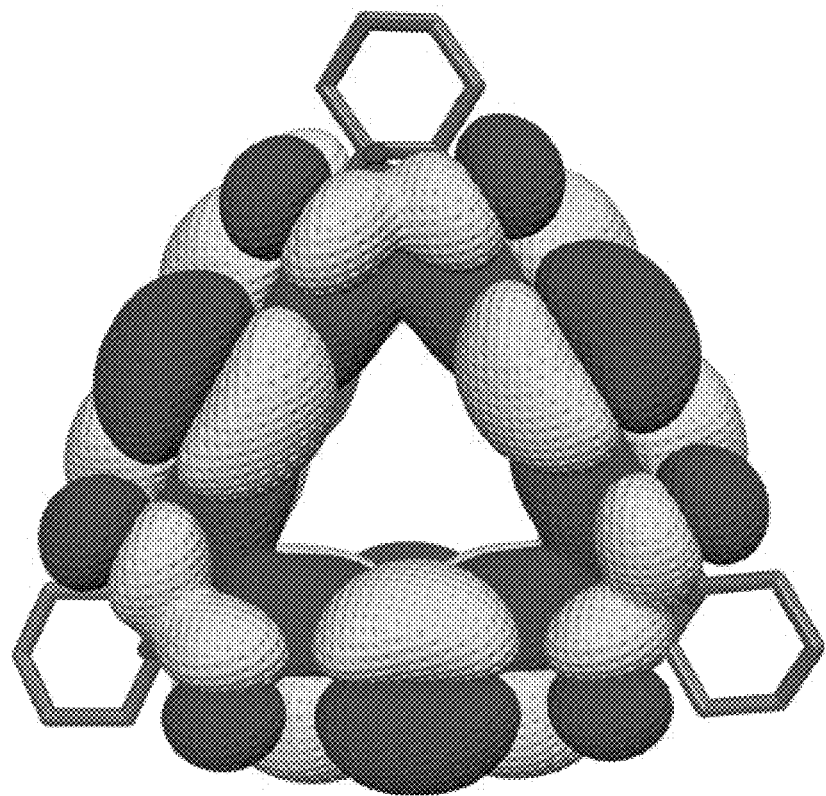
FIG. 1D depicts exemplary graphical representations of the DFT-calculated (B3LYP/6-31 G**) lowest unoccupied molecular orbital (LUMO) of (−)-NDI-Δ. Orbital isosurfaces are illustrated at 0.004 electrons $Bohr^{-3}$.

The molecular triangular prisms (−)- and (+)-NDI-Δ were synthesized in a single stereospecific step from two commercially available components, naphthalenetetracarboxylic dianhydride (1) and (RR) or (SS)-trans-1,2-cyclohexanediamine (2), in 25 and 23% yields, respectively (see FIG. 1A). The high symmetry of both (−)- and (+)-NDI-Δ is reflected by the relative simplicity of the $^1$H NMR spectra for the compounds, which show only two sets of signals for the 12 NDI protons. The rigid molecular structures of (−)- and (+)-NDI-Δ also lead to strong peaks in the circular dichroism (CD) spectra (see FIG. 1B). Both enantiomers of NDI-Δformed crystals from MeOH/CH$_2$Cl$_2$ solutions suitable for single-crystal X-ray diffraction analyses. The crystal structures (for example, for (−)-NDI-Δ shown in FIG. 1) confirm the rigid geometries of the hollow, equilateral, triangular prisms with a base-to-apex distance of about 1.0 nm. The faces of the NDI units in (−)-NDI-Δ, and also in (+)-NDI-Δ, are arranged with respect to each other in an orthogonal fashion, resembling the faces of triangular prisms. These rigid three-dimensional frameworks therefore constitute a unique geometrical arrangement of the NDI molecular orbitals for cyclic through-space electron sharing.

The electron-sharing hypothesis is supported by density functional theory (DFT) calculations that reveal the presence of delocalized frontier molecular orbitals in (−)-NDI-Δ. The highly delocalized LUMO of (−)-NDI-Δ is populated with one electron in [(−)-NDI-Δ]$^{•-}$ radical anion, resulting in a SOMO which resembles the LUMO of (−)-NDI-Δ closely in shape (see FIG. 1D). This result suggests that the unpaired electron in [(−)-NDI-Δ]$^{•-}$ is shared among all three NDI-units of the triangular prism, thus constituting a rare example of a purely organic mixed-valence radical in which the unpaired electron is surrounding a triangular cavity.

Figure 2:
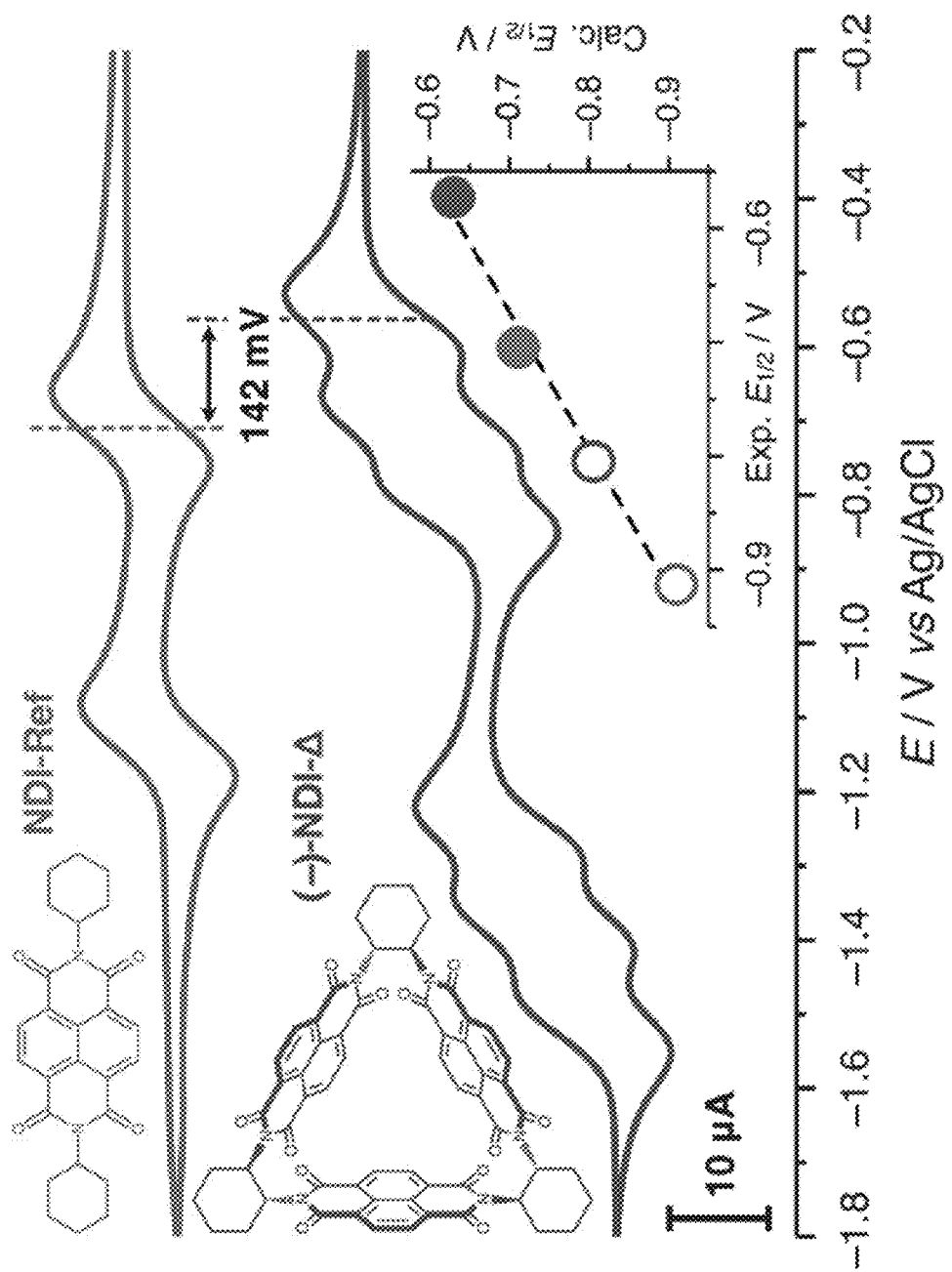
FIG. 2 depicts exemplary cyclic voltammograms (CVs) of a reference NDI compound (NDI-Ref) with cyclohexyl substituents (red curve) and (−)-NDI-Δ (blue curve) recorded (scan rate 50 $mVs^{-1}$) using a glassy carbon electrode. All of the experiments were performed at 298 K in argon-purged $CH_2Cl_2$ solutions (0.5 mm) with 0.1 m [$Bu_4N$][$PF_6$] as the supporting electrolyte. The inset shows the correlation between the DFT-calculated and the experimental half-wave potentials ($E_{1/2}$ vs. Ag/AgCl) for the first reductions of (−)-NDI-Δ (blue), NDI-Ref (red), and the corresponding compounds with all of the NDI groups replaced with pyromellitic diimide (PMI) functional groups. A linear fit to the data (γ=1.20 x+0.16 V) gave a coefficient of correlation ($R^2$) of 0.99.

Comparison of the cyclic voltammogram (CV) of (−)-NDI-Δ with that of a NDI reference compound (NDI-Ref) provides experimental evidence for the DFT-predicted cyclic electron sharing in (−)-NDI-Δ (see FIG. 2). While the CV of NDI-Ref possesses two sequential one-electron cathodic waves, observed at −709±5 and −1131±9 mV vs. Ag/AgCl, corresponding to the formation of the [NDI-Ref]$^{•-}$ radical anion and the [NDI-Ref]$^{•−}$ dianion, respectively, the CV of (−)-NDI-Δ reveals a dramatic splitting into six distinct reversible one-electron waves. This observation indicates that electronic communication between the three equivalent NDI redox centers is occurring within the triangular molecular prisms. Furthermore, the potential ($E_1$=−567±7 mV), corresponding to the first reduction of (−)-NDI-Δ is shifted by 142 mV towards more positive potentials compared to the $E_1$ of NDI-Ref. Similar shifts in redox potentials have been observed previously for covalently bonded, parallel π-π stacked NDI- and PDI-derivatives, which also display through-space electron sharing. The observed shift in redox potentials has also been rationalized quantitatively by DFT calculations employing a continuum solvent model with the B3LYP-functional, that is, the same functional used to compute the frontier molecular orbitals of (−)-NDI-Δ]. The good correlation observed (FIG. 2, inset) between the DFT-calculated and the experimental reduction potentials for (−)-NDI-Δ, NDI-Ref, (+)-PMI-Δ, and PMI-Ref add further credibility to the DFT-description of the (−)-NDI-Δ frontier molecular orbitals.

Figure 3A:
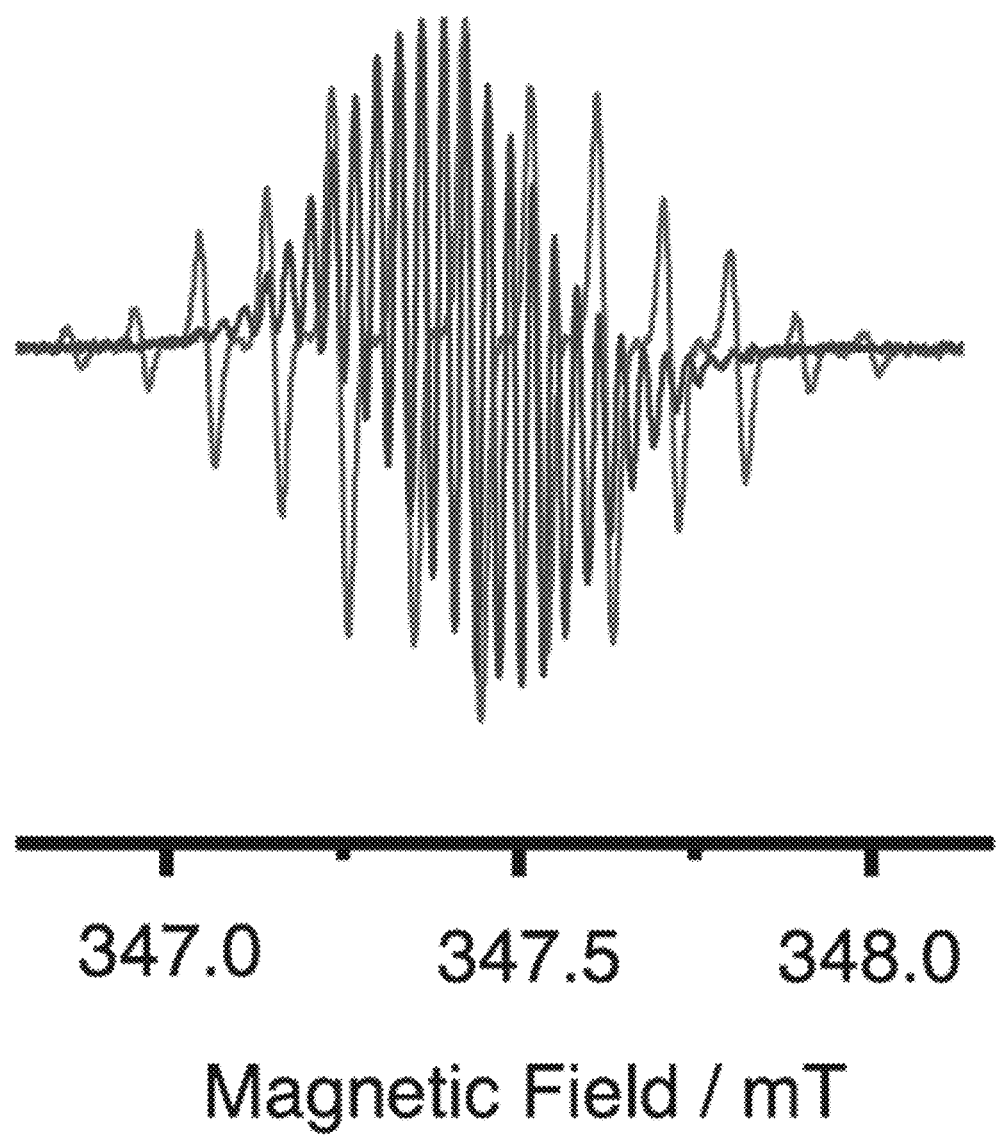
FIG. 3A depicts exemplary cw-EPR spectra of NDI-Ref (red curve) and (−)-NDI-Δ(blue curve) after reduction with 1.0 equiv of cobaltocene ([$CoCp_2$]). All of the spectra were recorded in $CH_2Cl_2$ (0.3 mm) at 265 K. The decrease in the EPR-linewidth for [(−)-NDI-Δ]$^{•−}$ by a factor of about 1.75 indicates sharing of the unpaired electron over all three NDI units.
Figure 3B:
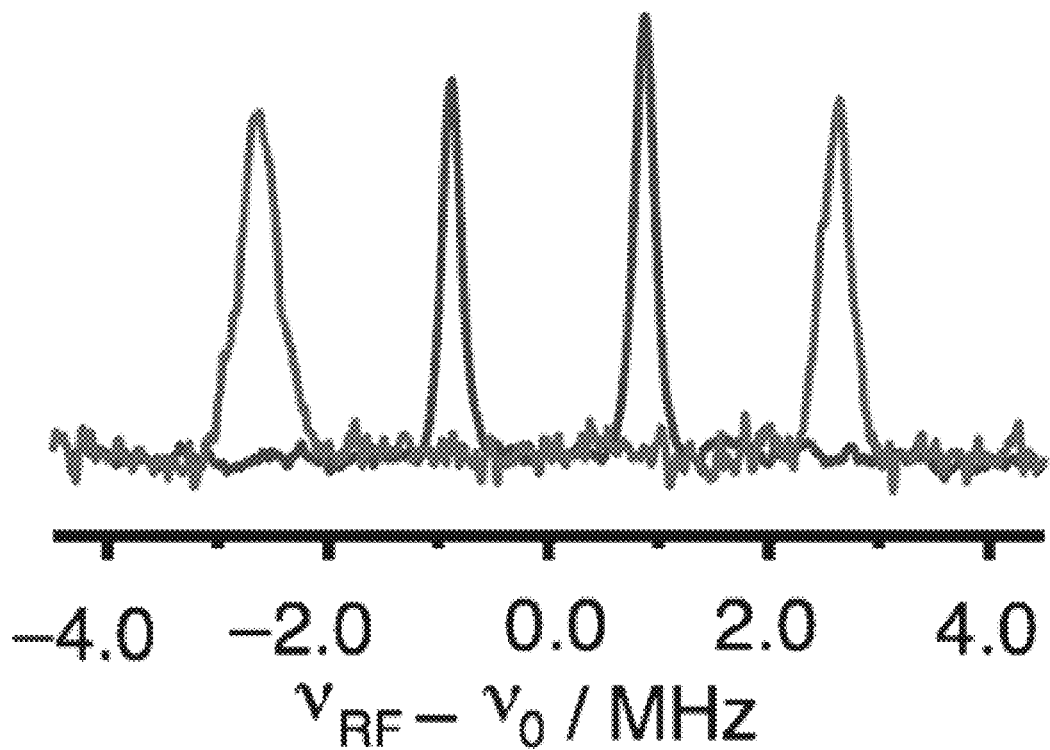
FIG. 3B depicts exemplary cw-ENDOR spectroscopy of NDI-Ref (red curve) and (−)-NDI-Δ (blue curve) after reduction with 1.0 equiv of cobaltocene ([$CoCp_2$]). The spectra were recorded in $CH_2Cl_2$ (0.3 mm) at 265 K. In the case of [(−)-NDI-Δ]$^{•−}$, the ENDOR spectrum shows a near-perfect one-third reduction of the proton hyperfine interactions, thereby confirming the decrease in EPR-linewidth observed in FIG. 3A.

While the UV/Vis spectrum of [(−)-NDI-Δ]$^{•-}$ also hints at electronic communication between the NDI units in the triangular prisms, even stronger experimental evidence for electron sharing in [(−)-NDI-Δ,]$^{•-}$ is provided by continuous wave (cw) electron paramagnetic resonance (EPR) and electron-nuclear double resonance (ENDOR) spectroscopies. When compared to the EPR spectrum of [NDI-Ref]$^{•-}$, that of [(−)-NDI-Δ]$^{•-}$ shows a decrease in line-width by a factor of 1.75 at 265K (FIG. 3A). This result is in good agreement with EPR theory for electron-delocalized systems, which predicts a reduction in EPR line-width by √n=1.73 for sharing of an electron by three (n=3) NDI units. Moreover, the proton hyperfine splittings in the cw-ENDOR spectra for the mono-radical anion [(−)-NDI-Δ]$^{•-}$ are also reduced by about a factor of three (FIG. 3B) when compared with the reference compound, providing yet further evidence for the sharing of the unpaired electron among the three symmetrically equivalent NDI subunits.

Figure 4A:
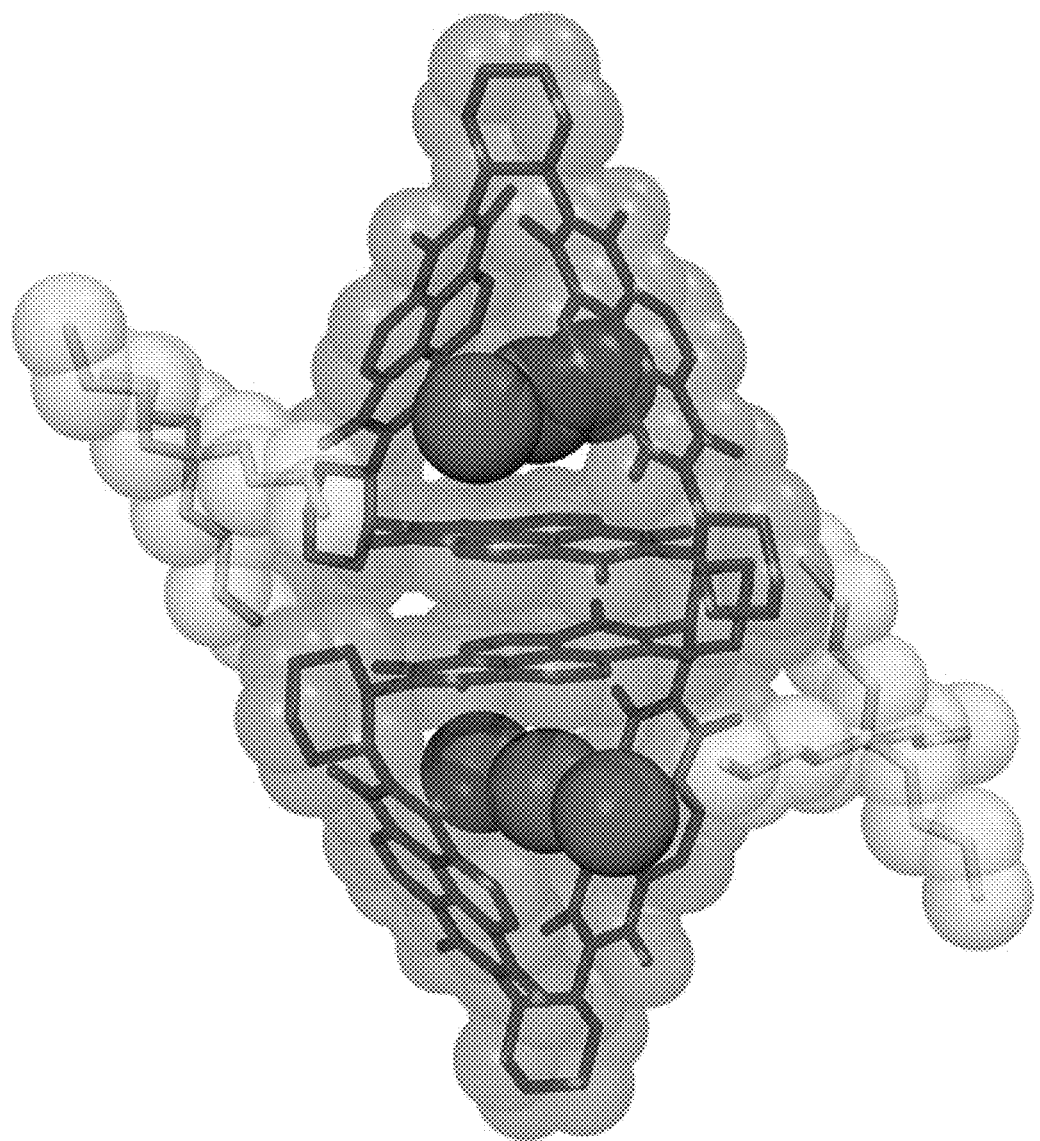
FIG. 4A depicts exemplary space-filling and graphical representations of the single-crystal X-ray superstructure of (−)-NDI-Δ with [$Bu_4N$][$I_3$] that shows a face-to-face π-stacked dimer, which is further stabilized with electrostatic and [C—H . . . O] interactions. Note that the superstructures of the NDI-Δ molecules without [$Bu_4N$][$I_3$] did not exhibit any π-stacking.
Figure 4B:
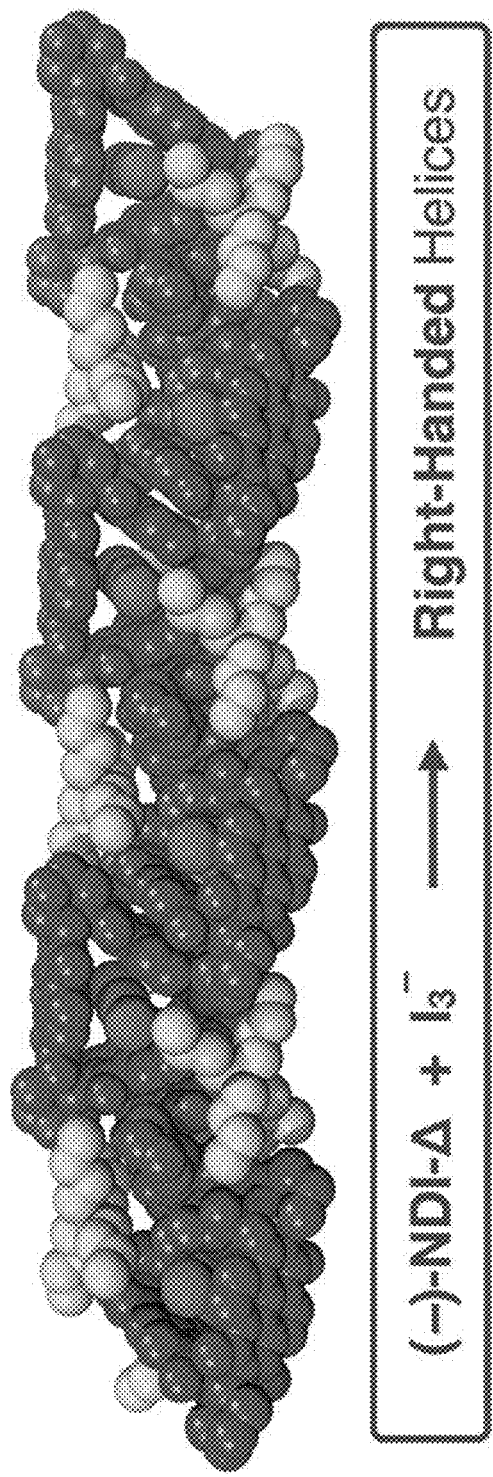
FIG. 4B depicts an exemplary space-filling representation of the right-handed, π-stacked supramolecular (P)-helices present in the solid-state superstructure of (−)-NDI-Δ.
Figure 4C:
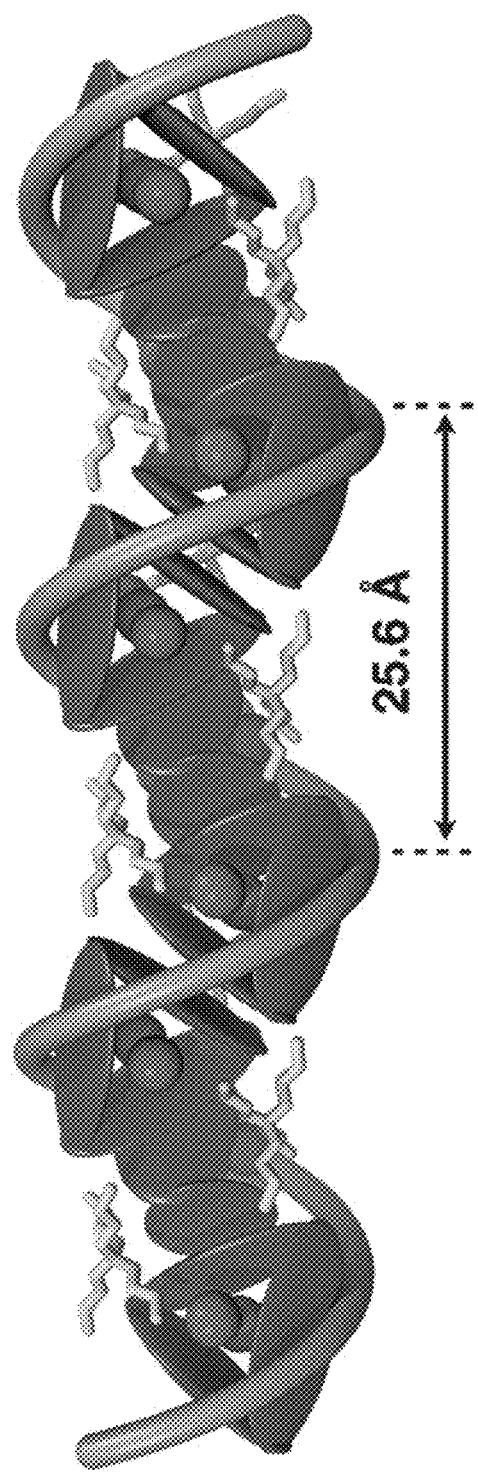
FIG. 4C depicts an exemplary graphical representation of the right-handed, π-stacked supramolecular (P)-helices present in the solid-state superstructure of (−)-NDI-Δ. In the case of (+)-NDI-Δ, the corresponding left-handed (M)-helices were formed stereospecifically. In both FIGS. 4B and 4C, (−)-NDI-Δ molecules are illustrated in blue, $I_3^-$ anions in purple, and $Bu_4N^+$ counterions in yellow. The helical nature of the stacked wires is illustrated on overlaying a light-blue helix. Hydrogen atoms are omitted for the sake of clarity.

The fact that electronic communication between the redox centers in (−)- and (+)-NDI-Δ increases the electron-affinity of the NDI units in the prisms, as shown by the CV data, should in turn also result in enhanced charge-transfer interactions with anions in the context of anion-π interactions. The tubular, electron-deficient cavities of (−)- and (+)-NDI-Δ could provide an ideal electronic and geometrical fit for the accommodation of the linear $I_3^-$ anion. To test this hypothesis, the (−)-NDI-Δ host was titrated with solutions of [Bu$_4$N][I$_3$] in CD$_2$Cl$_2$ and the binding constant ($K_a$) was evaluated by $^1$H NMR spectroscopy. Employing a 1:1 binding model, which was confirmed by a Job Plot, a modest $K_a$ value of 25±2 L mol$^{-1}$ was determined for the binding of $I_3^-$ by the (−)-NDI-Δ host. Structural evidence for the binding of $I_3^-$ inside the cavities of (−)- and (+)-NDI-Δ was obtained by single-crystal X-ray diffraction. Slow vapor diffusion of n-hexane into 1,2-dibromoethane solutions of (−)- and (+)-NDI-Δ, containing [Bu$_4$N][I$_3$], resulted in brown single crystals, which were found to be inclusion complexes of $I_3^-$ anions located inside (−)- and (+)-NDI-Δ, respectively. The solid-state super-structures (FIG. 4A) reveal that the linear $I_3^-$ anions almost completely fill up the tube-shaped cavities of the triangular molecular prisms, with anion-π distances of about 3.8 Å. With the $I_3^-$ anions buried completely inside the triangular prisms, there is no space for the Bu$_4$N$^+$ cations to reside close to the anions, leading to ion-pair separation upon guest binding. In the present case, it is clear that anion-π interactions within a neutral host are therefore able to break up ion-pairing in non-polar solvents, highlighting the significance of such supramolecular interactions inside a tri-angular prismatic cavity. The solid-state superstructures of (−)- and (+)-NDI-Δ also indicate that the formation of the $I_3^-$ inclusion complexes with (−)- and (+)-NDI-Δ leads to dramatic changes in the extended supramolecular interactions between the triangular prisms themselves. When they bind $I_3^-$ anions, π-π stacking of the triangular prisms is observed in the solid state (FIG. 4A), wherein two NDI units of each prism stack face-to-face with their neighbors at a near-perfect π-π stacking distance of about 3.4 Å with a cross-angle of 60°. On examining the packing in the solid state of the empty triangles, no π-π stacking is detected, indicating that the binding of $I_3^-$ seems to induce this extended supramolecular phenomenon. The anion-induced π-π stacking of the triangular prisms (FIG. 4B, C) leads to the stereocontrolled formation of single-handed helices, with every three triangles constituting one pitch of the helix with a repeat of 25.6 Å. The helicity of the resulting super-structures is controlled by the inherent chirality of the NDI-Δ prisms themselves; that is, while the (−)-NDI-Δ prisms form only right-handed (P)-helices in the solid-state, exclusively left-handed (M)-helices are formed from the corresponding (+)-enantiomer.

Solvent-Directed Assembly of NDI-Δ Nanotubes

Figure 5:
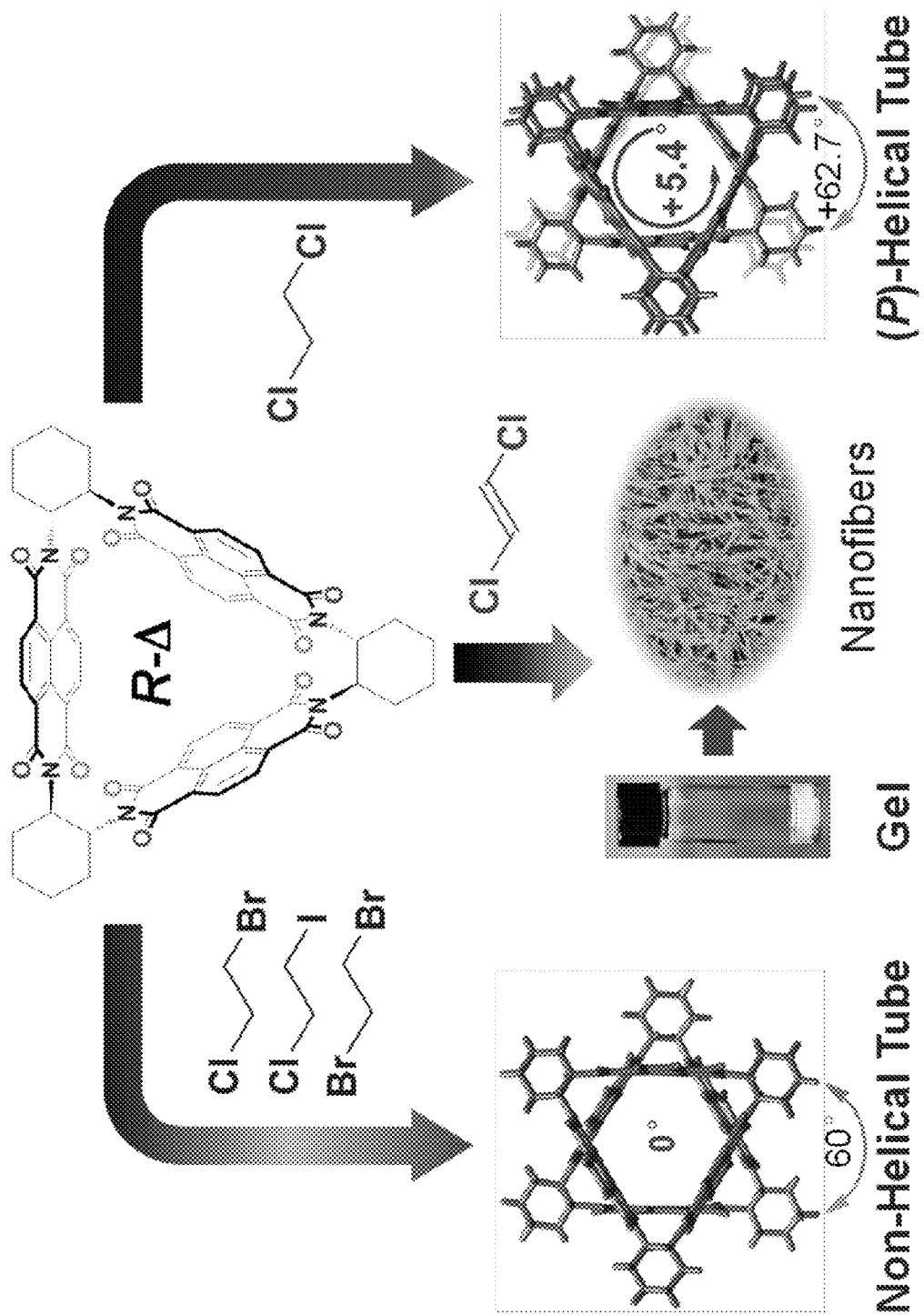
FIG. 5 depicts a schematic representation of three different assembly outcomes of (−)-NDI-Δ ("R-Δ") employing different DXE molecules. Middle: Gel specifically formed from R-Δ with (E)-DCE. Left: Non-helical tubes formed from R-Δ with DBA, CBA, and CIA. Right: (P)-Helical tube specifically formed from R-Δ with DCA.
Figure 6:
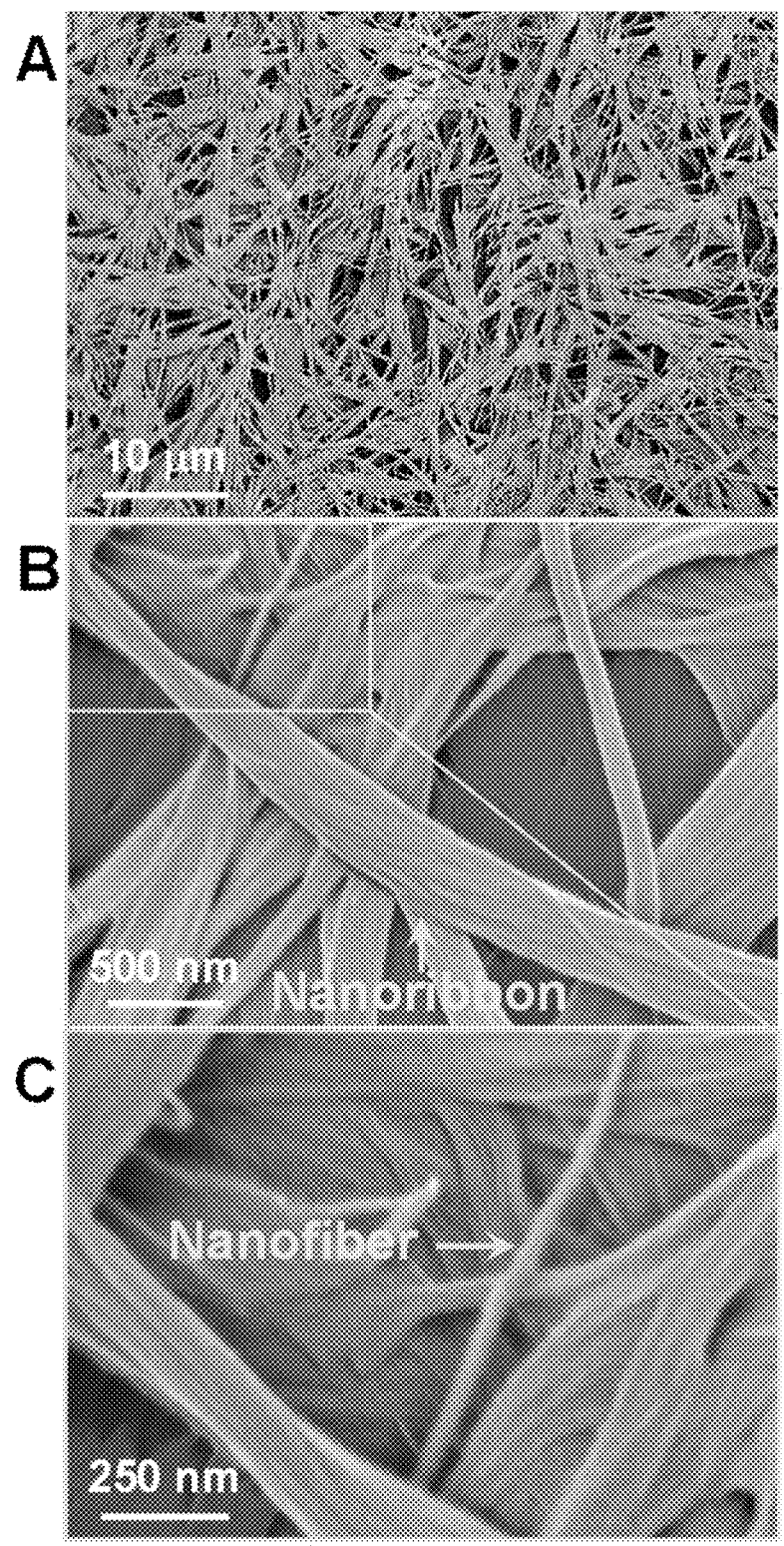
FIG. 6A depicts morphologies of the xerogel sample of (−)-NDI-Δ ("R-Δ") with (E)-DCE by SEM, wherein a large-scale network intertwined from nanoribbons.
FIG. 6B depicts an exemplary SEM of (−)-NDI-Δ ("R-Δ") with (E)-DCE showing nanoribbons formed by the aggregation of small nanofibers.
FIG. 6C depicts an exemplary SEM of (−)-NDI-Δ ("R-Δ") with (E)-DCE showing nanoribbons formed by the aggregation of small nanofibers.
Figure 7:
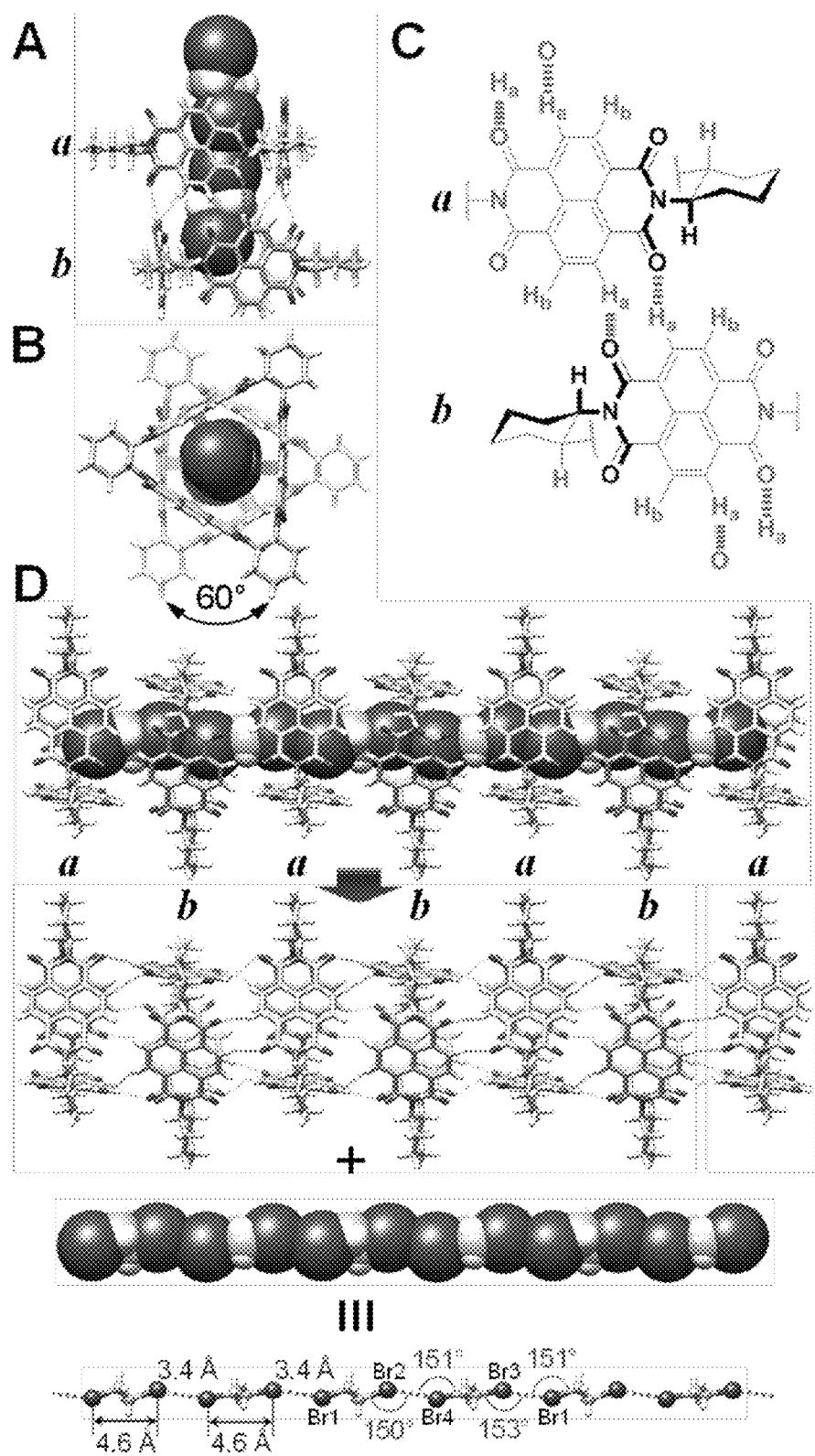
FIG. 7A depicts exemplary single crystal X-ray superstructure of DBA⊂R-Δ presented in tubular and space-filling formats, wherein a side-on view showing the relative orientation of two R-Δ a and b is presented.
FIG. 7B depicts an exemplary top view showing that the coaxial DBA chain (space filling) is stabilized through latitudinal [B . . . π] interaction (magenta hatched lines).
FIG. 7C depicts exemplary schematic views of the [C—H . . . O] interactions (magenta hatched lines) between R-Δ units a and b as well as the relative positions of the diastereotopic NDI protons $H_a$ (cis) and $H_b$ (trans) to the adjacent protons on the stereogenic center of the 1,2-cyclohexano moieties.
FIG. 7D depicts an exemplary schematic illustration of the one-dimensional superstructure in which the R-Δ tori form a continuous channel occupied by a [Br . . . Br]-bonded DBA chain. C, tan; H, white; O, red; N, blue; Br, brown. Hydrogen and halogen bonds are depicted as magenta hatched lines.
Figure 8:
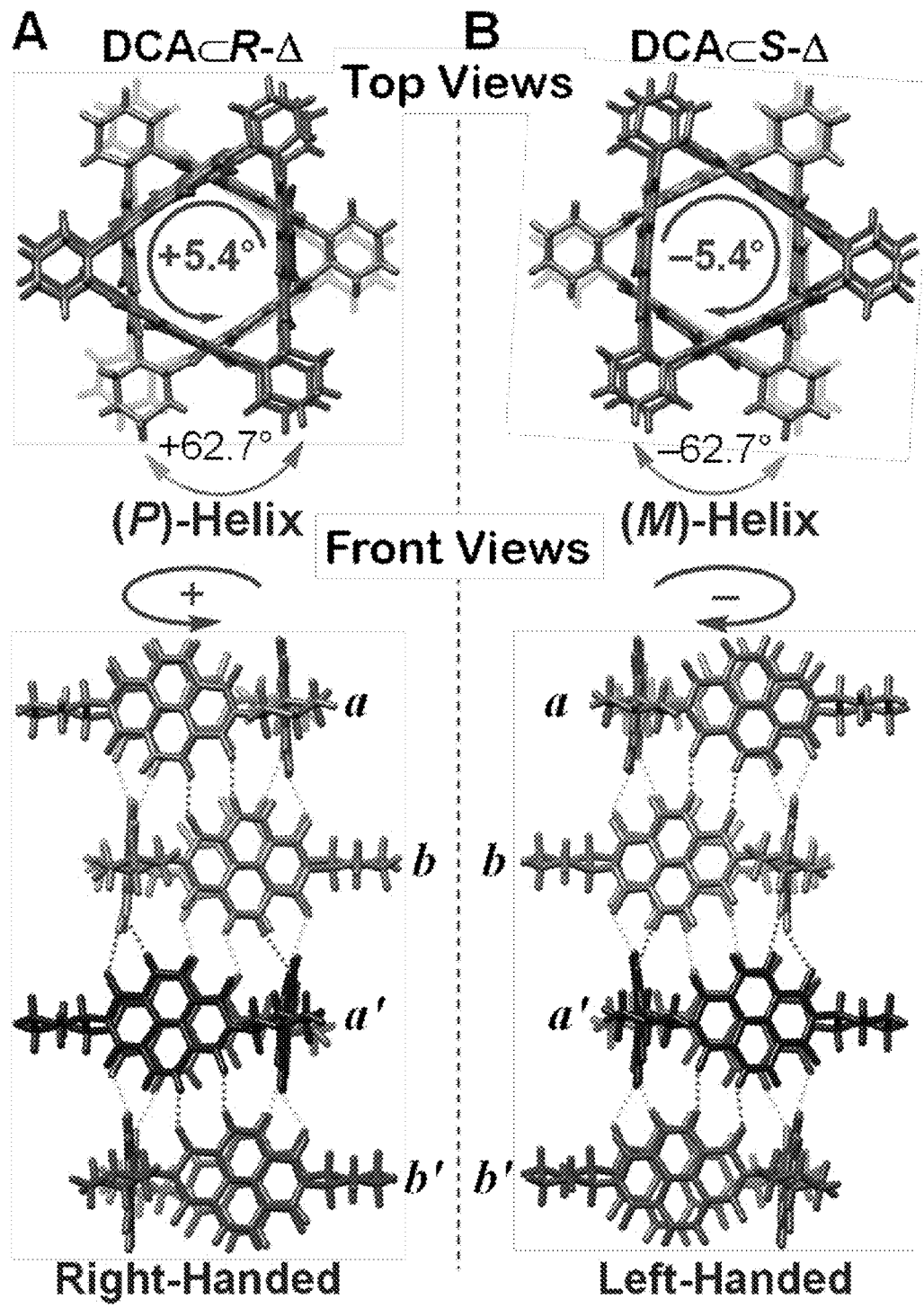
FIG. 8A depicts an exemplary single crystal X-ray superstructure of DCA⊂R-Δ presented in tubular format, wherein the top and front views of the left-handed helical DCA⊂R-Δ are shown.
FIG. 8B depicts an exemplary single crystal X-ray superstructure of DCA⊂S-Δ presented in tubular format, wherein the top and front views of right-handed helical DCA⊂S-Δ are shown.
Figure 9:
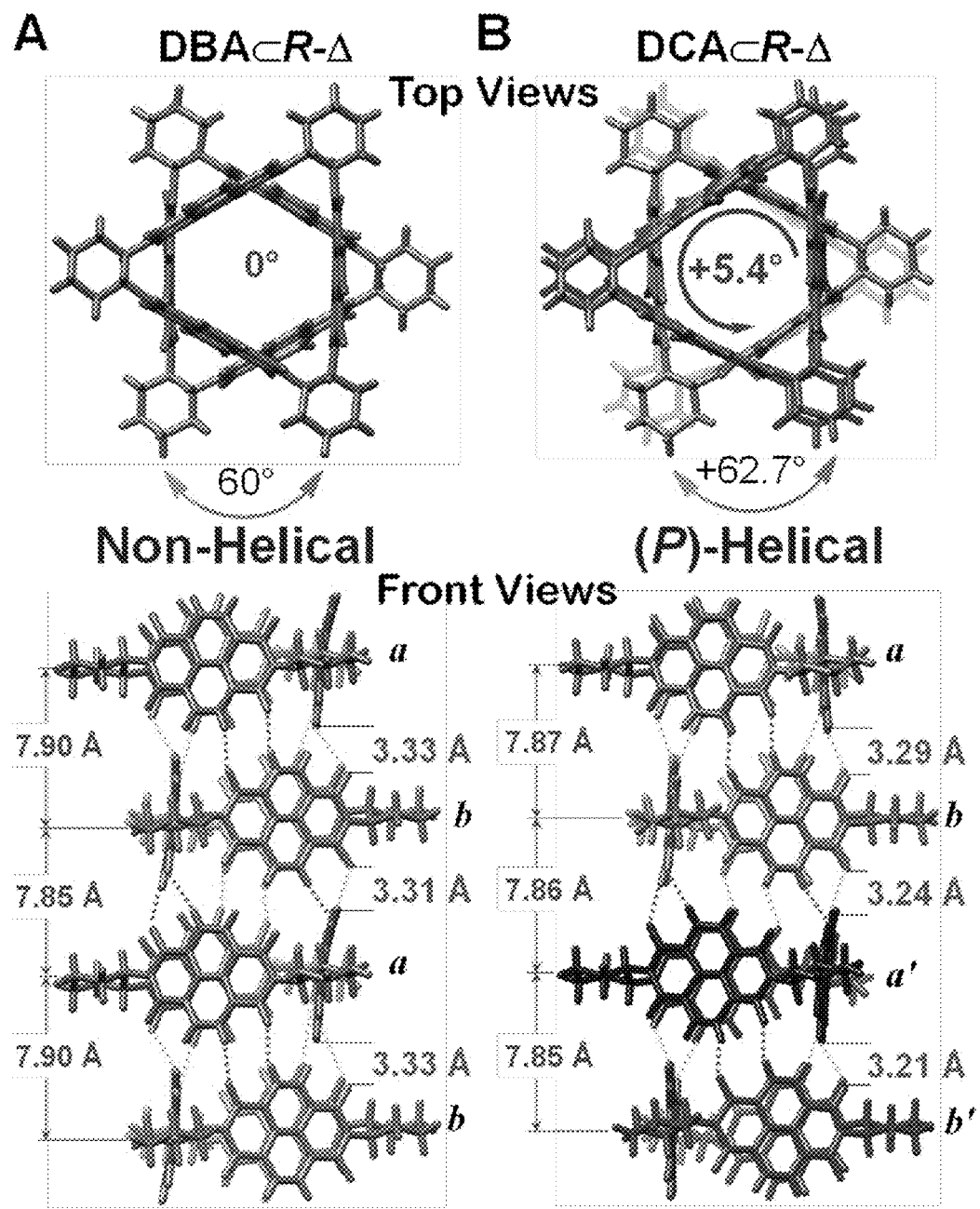
FIG. 9A depicts an exemplary single crystal X-ray superstructure of a non-helical tetrameric unit of DBA⊂R-Δ.
FIG. 9B depicts an exemplary single crystal X-ray superstructure of (P)-Helical tetrameric DCA⊂R-Δ. For FIGS. 9A and 9B, non-equivalent R-Δ units are highlighted with different colors. Green arrows indicate the net rotation angles between the NDI-Δ units a and a' as well as b and b'. Double-colored arrows show the relative rotation angle between the neighboring NDI-Δ units. Hydrogen bonds are depicted as magenta hatched lines and mean $d_{C\ldots O}$ are present magenta color. DBA molecules inside the channel of DBA⊂R-Δ are omitted for the sake of clarity.

The selection of DXEs can direct highly specific assembly of a diverse range of supramolecular nanotubes of NDI-Δ. Referring to FIG. 5, NDI-Δ can be assembled to form (i) an organogel which is made up of intertwining supramolecular nanotubes in a specific solvent—namely, (E)-1,2-dichloroethene ((E)-DCE), (ii) non-helical supramolecular nanotubes in the solid states under the influence of templating [X . . . X]-bonded BrCH$_2$CH$_2$Br (DBA), ClCH$_2$CH$_2$Br (CBA), or ClCH$_2$CH$_2$I (CIA) supramolecular chains, and (iii) (P)- and (M)-helical supramolecular nanotubes in the solid state as a result of the columnar stacking of the (−)- and (+)-NDI-Δ macrocycles (denoted herein as "R-Δ" and "S-Δ", respectively), under the directing influence of [Cl . . . Cl]-bonded ClCH$_2$CH$_2$Cl (DCA) supramolecular chains. FIG. 6 depicts morphologies of the xerogel sample of R-Δ with (E)-DCE by SEM, wherein a network intertwined from nanoribbons and individual nanofibers are shown. FIG. 7 depicts exemplary single crystal X-ray superstructure of DBA⊂R-Δ presented in tubular and space-filling formats. FIG. 8 depicts exemplary single crystal X-ray superstructures of DCA⊂R-Δ and DCA⊂S-Δ presented in tubular format. FIG. 9 depicts exemplary single crystal X-ray superstructures of a non-helical tetrameric unit of DBA⊂R-Δ and a (P)-Helical tetrameric DCA⊂R-Δ.

Applications

In a first aspect, a redox-active triangular prism is provided. The redox-active triangular prism includes a plurality of pure enantiomers selected from a group consisting of (−)-NDI-Δ and (+)-NDI-Δ. In a first respect, the plurality of pure enantiomers forms a structure having a central cavity. In a second respect, the central cavity comprises sufficient dimensions to accommodate a guest anion. In a third respect, the structure is stabilized through π-π interactions among adjacent members of the plurality of pure enantiomers upon binding a guest anion. In a fourth respect, the structure comprises a redox activity of greater than two reversible one-electron cathodic waves. In some respects, the plurality of pure enantiomers is (−)-NDI-Δ. In these respects, the plurality of pure enantiomers form a structure having a central cavity, wherein the structure is selected from a group consisting of a right-handed, supramolecular (P)-helix, an organogel, a non-helical supramolecular nanotube and a (P)-helical supramolecular nanotube. In those respects where the structure is an organogel, the organogel includes a plurality of intertwining supramolecular nanotubes. In other respects, the plurality of pure enantiomers consists of (+)-NDI-Δ. In these respects, the plurality of pure enantiomers forms a structure having a central cavity, wherein the structure is selected from a group consisting of a left-handed, supramolecular (M)-helix and a (M)-helical supramolecular nanotube.

In a second aspect, a method of making a redox-active triangular prism is provided. The method includes several steps. The first step includes preparing a mixture that includes naphthalene-tetracarboxylic dianhydride, a pure enantiomer selected from a group consisting of (RR)-trans-1,2-cyclohexanediamine ((RR)-2) and (SS)-trans-1,2-cyclohexanediamine ((SS)-2) and a solvent. The second step includes incubating the mixture at a temperature above ambient temperature. In some respects, the solvent includes an organic solvent. In some of these respects, the organic solvent includes dimethylformide.

In some of these respects, the pure enantiomer is (RR)-trans-1,2-cyclohexanediamine. In a further elaboration of these respects, the method includes the additional steps of purifying (−)-NDI-Δ product by chromatography and precipitating (−)-NDI-Δ. With respect to preparing solvent-templated supermolecular structures, the method is adapted to include additional steps. These steps include preparing a solution comprising (−)-NDI-Δ and a solvent and diffusing n-hexane in the solution to form complexes comprising solvent and (−)-NDI-Δ. In these instances, the solvent is selected from a group consisting of (E)-1,2-dichloroethene, BrCH$_2$CH$_2$Br, ClCH$_2$CH$_2$Br, ClCH$_2$CH$_2$I and ClCH$_2$CH$_2$Cl.

In other respects, the pure enantiomer is (SS)-trans-1,2-cyclohexanediamine. In a further elaboration of these respects, the method includes the additional steps of purifying (+)-NDI-Δ product by chromatography and precipitating (+)-NDI-Δ. With respect to preparing solvent-templated supramolecular structures, the method is adapted to include additional steps. These steps include preparing a solution comprising (+)-NDI-Δ and a solvent and diffusing n-hexane in the solution to form complexes comprising solvent and (+)-NDI-Δ. In these instances, the solvent is selected from a group consisting of (E)-1,2-dichloroethene, $BrCH_2CH_2Br$, $ClCH_2CH_2Br$, $ClCH_2CH_2I$ and $ClCH_2CH_2Cl$.

In a third aspect, an electrode comprising a redox-active triangular prism is provided. The redox-active triangular prism includes a plurality of pure enantiomers selected from a group consisting of (−)-NDI-Δ and (+)-NDI-Δ, or a solvent-crystalline complex thereof.

EXAMPLES

The invention will be more fully understood upon consideration of the following non-limiting examples, which are offered for purposes of illustration, not limitation.

Example 1

Materials and Methods

Reagents were purchased from Aldrich Chemical Company and were used without further purification. Cobaltocene ($CoCp_2$) was handled and stored in an Argon Glovebox. While small amounts of (RR)- and (SS)-trans-1,2-cyclohexanediamine [(RR)- and (SS)-2] were also purchased from Aldrich Chemical Company, large amounts of enantiopure (RR)-2 were obtained by resolving racemic trans-1,2-cyclohexanediamine with L-(+)-tartaric acid, as described in the literature, Tetrabutylammonium triiodide ([$Bu_4N$][$I_3$]), bis(cyclohexyl)naphthalene-tetracarboxylic diimide (NDI-Ref), bis(cyclohexyl)pyromellitic diimide (PMI-Ref), and the triangular macrocycle (+)-PMI-Δ with pyromellitic diimide residues were synthesized and purified according to previously reported procedures. Solvents (THF, DMF, $CH_2Cl_2$) were dried using a commercial solvent purification system (SG Water, Inc.). All reactions were performed under a nitrogen atmosphere, unless stated otherwise. Analytical thin-layer chromatography (TLC) was carried out using glass plates, precoated with silica gel 60 containing fluorescent indicator (Whatman LK6F). The plates were inspected by UV light (254 nm) and/or $KMnO_4$ stain. Flash chromatography was carried out using silica gel 60 (Silicycle) as the stationary phase. UV-Vis-NIR Absorbance spectra were recorded using a Perkin Elmer LAMBDA 1050 double beam, double monochromator, ratio-recording spectrometer. Measurements of circular dichroism (CD) were carried out on a Jasco J-815 spectrometer. Nuclear magnetic resonance (NMR) spectra were recorded at 298 K, unless stated otherwise, on Bruker Avance III 500 and 600 MHz spectrometers, with working frequencies of 499.373 and 600.168 MHz for $^1H$, and 125.579 and 150.928 MHz for $^{13}C$ nuclei, respectively. Chemical shifts are reported in ppm relative to the signals corresponding tetramethylsilane (TMS: δ=0.00 ppm). Coupling constants are recorded in Hertz (Hz). All $^{13}C$ NMR spectra were recorded with the simultaneous decoupling of proton nuclei. The following abbreviations were used to identify signal multiplicities: s, singlet; d, doublet; t, triplet; b, broad peaks; m, multiplet or overlapping peaks. High-resolution electrospray ionization (ESI) mass spectra were obtained on an Agilent 6210 LC-TOF high-resolution mass spectrometer. Low-resolution ESI-MS spectra were recorded on a Thermo Finnigan LCQ™ Advantage mass spectrometer. Cyclic voltammetry (CV) experiments were performed on a Gamry Multipurpose instrument (Reference 600), instrument interfaced to a PC, using a glassy carbon-working electrode (0.071 $cm^2$, Cypress system). The electrode surface was polished routinely with 0.05 $\mu m^2$ alumina-water slurry on a felt surface immediately before use. The counter electrode was a Pt coil and the reference electrode was a AgCl coated Ag wire. The Ag/AgCl reference electrode was calibrated against ferrocene ($E_{1/2}$=520 mV) and was found to be stable during the course of the measurements. Spectroelectrochemical (SEC) experiments were carried out using a custom-built optically-transparent thin layer electrochemical (OTTLE) cell with an optical path of 2 mm, using a Pt grid as working electrode, a Pt wire as counter electrode and a Ag wire pseudo-reference electrode. EPR and ENDOR spectra were acquired with a Bruker Elexsys E580 spectrometer, fitted with the DICE ENDOR accessory, an EN801 resonator, and an ENI A-500 RF power amplifier.

Applied RF powers ranged from 250 to 300 W across the 4 MHz scanned range, and the microwave power ranged from 0.6 to 100 mW. The sample temperatures were controlled by a liquid nitrogen flow system. Samples were reduced using cobaltocene ($CoCp_2$) as the chemical reductant and loaded into 1.4 mm I.D. quartz tubes, which were sealed with epoxy resin in an argon filled glovebox. A spline fit baseline correction was applied to the ENDOR spectra following integration.

Example 2

Synthesis of (−)-NDI-Δ and (+)-NDI-Δ, and Organogels (−)-NDI-Δ. A warm solution of (RR)-trans-1,2-cyclohexanediamine [(RR)-2, 1.71 g, 15.0 mmol] in anhydrous DMF (10 ml) was added quickly to a solution of naphthalene-tetracarboxylic dianhydride (1, 3.98 g, 14.8 mmol) in anhydrous DMF (200 ml) with vigorous stirring at 150° C. The resulting dark red reaction mixture was stirred at 150° C. for 5 h and the DMF was evaporated under reduced pressure (~3 mbar) at 75° C. The deep red residue was dissolved in $CH_2Cl_2$ and purified by flash column chromatography over silica gel ($CH_2Cl_2/Me_2CO$, 0-10% $Me_2CO$), followed by precipitation of the product with MeOH to afford pure (−)-NDI-Δ (1.27 g, 1.2 mmol) in 25% yield as a slightly yellow solid. $^1H$ NMR (500 MHz, $CDCl_3$): δ=8.50 (d, J=7.8 Hz, 6H), 8.48 (d, J=7.8 Hz, 6H), 6.23 (dt, J=8.2, 2.2 Hz, 6H), 2.69-2.32 (m, 6H), 2.17-1.87 (m, 12H), 1.84-1.47 (m, 6H). $^{13}C$ NMR (125 MHz, $CDCl_3$): δ=162.88, 162.58, 131.50, 130.90, 126.56, 126.22, 125.95, 54.03, 30.07, 25.87. HR-ESI-MS: calcd for $[M+Na]^+$ m/z=1061.2753. found 1061.2736.

(+)-NDI-Δ. The enantiomeric (+)-NDI-Δ (700 mg, 0.7 mmol) was obtained in 23% yield from naphthalenetetracarboxylic dianhydride (1, 2.32 g, 8.7 mmol) and (SS)-trans-1,2-cyclohexanediamine [(SS)-2, 1.0 g, 8.7 mmol] following the same procedure as that described above for (−)-NDI-Δ. The spectroscopic data were identical with those obtained for (−)-NDI-Δ, except for the CD spectrum, which was the mirror image of the one observed for the (−)-enantiomer.

Preparation of the organogel. A suspension of (−)-NDI-Δ ("R-Δ") (5 mg) in (E)-1,2-dichloroethene [(E)-DCE] (0.5 mL) was sonicated for 1 min. As the solid disappeared gradually, an off-white gel formed. The xerogel sample was prepared by drop-casting an as-synthesized gel on a silicon wafer followed by drying with a lyophilizer. SEM images were obtained using a Hitachi S-4800 FS-SEM.

Example 3

$^1$H NMR Titration Experiments and Job Plot

The $^1$H NMR titration was carried out by adding tetrabutylammonium triiodide ([Bu$_4$N][I$_3$] 100 mM, CD$_2$Cl$_2$) to a solution (0.267 mM, CD$_2$Cl$_2$) of (−)-NDI-Δ at room temperature. Upfield shifts of the NDI protons of the host were observed and used to determine the association constants ($K_a$). Dynafit, a program that employs nonlinear least-squares regression analysis was employed to fit the titration curve and determine a $K_a$ value for the complex. The $K_a$ value for the 1:1 complex formed between (−)-NDI-Δ and I$_3^-$ was found to be 25±2 M$^{-1}$ in CD$_2$Cl$_2$.

A Job plot was prepared following a $^1$HNMR titration to determine the stoichiometry of the host-guest complex between (−)-NDI-Δ and I$_3^-$ in CD$_2$Cl$_2$. The samples were prepared so that the total molar concentrations of compounds were 1.0 mM with respect to each sample: only the ratios of host to guest were altered. The chemical shift of one signal (that for the NDI protons) in the spectrum, which was followed as a function of the change (Δδ) in δ, multiplied by the mole fraction of host in solution, was plotted against the mole fraction of the host. The plot indicates that (−)-NDI-Δ and I$_3^-$ form a 1:1 complex in CD$_2$Cl$_2$.

Example 4

Single Crystal X-Ray Crystallography

Intensity data were collected in the cold gas stream of a Bruker Kappa APEX2 CCD area detector, equipped with a Cu K$_\alpha$ sealed tube with graphite. Single crystals of both (−)- and (+)-NDI-Δ were grown by slow vapor diffusion of MeOH into CH$_2$Cl$_2$ solutions, while co-crystals with [Bu$_4$N][I$_3$] were grown by slow vapor diffusion of n-hexane into 1,2-dibromoethane solutions. Crystallographic data (excluding structure factors) for these structures have been deposited with the Cambridge Crystallographic Data Centre as supplementary publication no. CCDC-958569, CCDC-958570, CCDC-958571 and CCDC-958572. These data can be obtained free of charge from The Cambridge Crystallographic Data Centre.

Crystal data for (−)-NDI-Δ. C$_{60.75}$H$_{43.5}$Cl$_{1.5}$N$_6$O$_{12}$, Mr=1102.69, colorless blocks, crystal size 0.096×0.061× 0.058 mm$^3$, cubic, space group I2$_1$3, a=b=c=29.5082(9) Å, V=25694(2) Å$^3$, Z=16, ρ$_{calc}$=1.140 mg/mm$^3$, T=99.97 K, R$_1$(F$^2$>2σF$^2$)=0.0505, wR$_2$=0.1353 (all data). Out of 44216 reflections, a total of 7043 were unique. The solvent masking procedure, as implemented in Olex2, was used to remove the electronic contribution of solvent molecules from the refinement. As the exact solvent content is not known, only the atoms used in the refinement model are reported in the formula here. Total solvent accessible volume/cell=8171.4 Å$^3$ [31.8%] Total electron count/cell=2079.8.

Crystal data for (+)-NDI-Δ. C$_{120}$H$_{90}$N$_{12}$O$_{27}$, Mr=2132.03, colorless blocks, crystal size 0.293×0.132× 0.094 mm$^3$, cubic, space group I2$_1$3, a=b=c=29.5156(12) Å, V=25713(3) Å$^3$, Z=8, ρ$_{calc}$=1.101 mg/mm$^3$, T=100.04 K, R/F$^2$>2σF$^2$)=0.0752, wR$_2$=0.2234 (all data). Out of 57758 reflections, a total of 7297 were unique. The solvent masking procedure, as implemented in Olex2, was used to remove the electronic contribution of solvent molecules from the refinement. As the exact solvent content is not known, only the atoms used in the refinement model are reported in the formula here. Total solvent accessible volume/cell=8354.7 Å$^3$ [32.5%] Total electron count/cell=243.8.

Crystal data for [Bu$_4$N][I$_3$⊂(−)-NDI-Δ]. C$_{94}$H$_{117}$Br$_2$I$_6$N$_8$O$_{12}$, M$_r$=2472.17, deeply colored blocks, crystal size 0.466×0.038×0.017 mm$^3$, trigonal, space group R3, a=b=32.0367(4), c=25.5838(4) Å, γ=120.00°, V=22740.0(7) Å$^3$, Z=9, ρ$_{calc}$=1.625 mg/mm$^3$, T=99.93 K, R/F$^2$>2σF$^2$)=0.0695, wR$_2$=0.1702 (all data). Out of 37385 reflections, a total of 15807 were unique. The solvent masking procedure, as implemented in Olex2, was used to remove the electronic contribution of solvent molecules from the refinement. As the exact solvent content is not known, only the atoms used in the refinement model are reported in the formula here. Total solvent accessible volume/cell=1384.4 Å$^3$ [6.1%] Total electron count/cell=581.6.

Crystal data for [Bu$_4$N][I$_3$⊂(+)-NDI-Δ]. C$_{94}$H$_{118}$Br$_2$I$_6$N$_8$O$_{12}$, M$_r$=2473.18, deeply colored blocks, crystal size 0.284×0.052×0.031 mm$^3$, trigonal, space group R3, a=b=32.0402(9), c=25.6102(9) Å, γ=120.00°, V=22768.5(15) Å$^3$, Z=9, ρ$_{calc}$=1.623 mg/mm$^3$, T=100.01 K, R$_1$ (F$^2$>2σF$^2$)=0.1220, wR$_2$=0.3159 (all data). Out of 15169 reflections, a total of 9596 were unique. The solvent masking procedure, as implemented in Olex2, was used to remove the electronic contribution of solvent molecules from the refinement. As the exact solvent content is not known, only the atoms used in the refinement model are reported in the formula here. Total solvent accessible volume/cell=1400.9 Å$^3$ [6.2%] Total electron count/cell=133.5.

NDI-Δ/DxE crystalline complexes. Single crystals of the NDI-Δ/DXE complexes, which were grown by slow vapor diffusion of n-hexane into solutions of (−)-NDI-Δ ("R-Δ") or (+)-NDI-Δ ("S-Δ") in 1,2-dihaloethane (ClCH$_2$CH$_2$Cl (DCA), BrCH$_2$CH$_2$Br (DBA), ClCH$_2$CH$_2$Br (CBA), or ClCH$_2$CH$_2$I (CIA)), were selected and mounted using oil (Infineum V8512) on a glass fiber and transferred to the cold gas stream cooled by liquid N$_2$. The X-ray crystal data were collected (Table 1) at 100 K using a Bruker Kappa APEX CCD area detector, equipped with a Cu—K$_\alpha$ microsource with MX optics.

TABLE 1

Crystallographic data and structural refinement details for DXE⊂NDI-Δ complexes

| Complex | DBA⊂R-Δ | DBA⊂S-Δ | DCA⊂R-Δ | DCA⊂S-Δ |
|---|---|---|---|---|
| Empirical formula | CH$_2$BrCH$_2$Br ⊂ (RRRRRR)-NDI-Δ | CH$_2$BrCH$_2$Br ⊂ (SSSSSS)-NDI-Δ | CH$_2$ClCH$_2$Cl ⊂ (RRRRRR)-NDI-Δ | CH$_2$ClCH$_2$Cl ⊂ (SSSSSS)-NDI-Δ |
| Crystal system | triclinic | triclinic | monoclinic | monoclinic |
| Space group | P1 | P1 | C2 | C2 |
| a /Å | 15.7472(10) | 15.7342(6) | 46.2752(15) | 46.8926(8) |
| b/Å | 16.1193(13) | 16.0668(6) | 16.1173(5) | 16.3192(3) |
| c/Å | 16.2046(12) | 16.1856(6) | 40.4255(14) | 40.7083(7) |
| α/° | 119.442(4) | 119.5499(16) | 90 | 90 |
| β/° | 100.225(3) | 100.2052(18) | 90.025(2) | 90.6571(12) |

TABLE 1-continued

Crystallographic data and structural refinement details for DXE ⊂ NDI-Δ complexes

| Complex | DBA ⊂ R-Δ | DBA ⊂ S-Δ | DCA ⊂ R-Δ | DCA ⊂ S-Δ |
|---|---|---|---|---|
| $\gamma/°$ | 92.957(4) | 92.9355(18) | 90 | 90 |
| $V/Å^3$ | 3478.6(5) | 3457.0(2) | 30150.6(17) | 31150.0(9) |
| Z | 2 | 2 | 16 | 16 |
| $\rho_{calc}$/mg mm$^{-3}$ | 1.530 | 1.540 | 0.959 | 0.886 |
| $\mu$/mm$^{-1}$ | 4.683 | 4.713 | 0.872 | 0.519 |
| F(000) | 1596 | 1596 | 9040 | 8640 |
| Crystal size/mm$^3$ | 0.245 × 0.076 × 0.038 | 0.142 × 0.098 × 0.055 | 0.382 × 0.156 × 0.09 | 0.402 × 0.217 × 0.07 |
| 2θ range for data collection | 5.78-122.324° | 5.78-129.78° | 2.18-101.1° | 4.37-130.348° |
| Index ranges | −17 ≤ h ≤ 17 | −17 ≤ h ≤ 18 | −45 ≤ h ≤ 46 | −54 ≤ h ≤ 54 |
|  | −18 ≤ k ≤ 15 | −10 ≤ k ≤ 18 | −14 ≤ k ≤ 16 | −19 ≤ k ≤ 19 |
|  | 0 ≤ l ≤ 18 | −18 ≤ l ≤ 15 | −39 ≤ l ≤ 40 | −47 ≤ l ≤ 47 |
| Reflections collected | 10617 | 13977 | 66099 | 156519 |
| Independent reflections | 10617 | 13977 | 26104[$R_{int}$ = 0.0384] | 51762[$R_{int}$ = 0.0594] |
| Data/restraints/parameters | 10617/1584/1641 | 13977/1593/1640 | 26104/6257/2881 | 51762/1/2809 |
| Goodness-of-fit on $F^2$ | 1.278 | 1.057 | 1.021 | 0.979 |
| Final R indices [I > 2σ(1)] | $R_1$ = 0.0968 | $R_1$ = 0.0525 | $R_1$ = 0.0651 | $R_1$ = 0.0523 |
|  | $wR_2$ = 0.2768 | $wR_2$ = 0.1458 | $wR_2$ = 0.1802 | $wR_2$ = 0.1349 |
| Final R indices [all data] | $R_1$ = 0.1084 | $R_1$ = 0.0543 | $R_1$ = 0.0850 | $R_1$ = 0.0765 |
|  | $wR_2$ = 0.2928 | $wR_2$ =0.1478 | $wR_2$ = 0.1923 | $wR_2$ = 0.1440 |
| Largest diff. peak/hole (e Å$^{-3}$) | 1.370/−0.862 | 1.163/−0.559 | 0.288/−0.258 | 0.172/−0.220 |
| CCDC Number | 1019483 | 1019484 | 1019481 | 1019482 |

Figure 10:
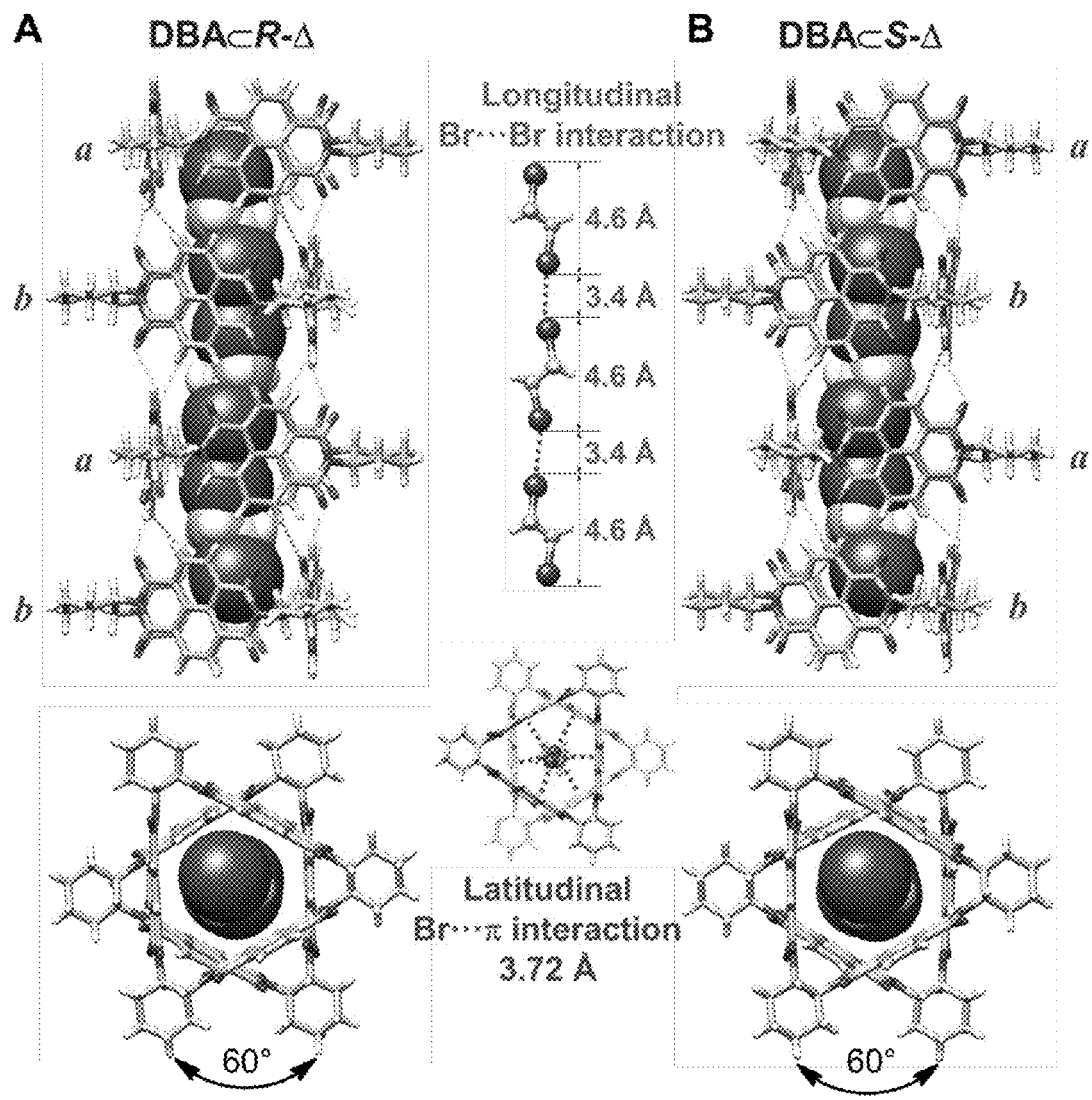
FIG. 10A depicts a single-crystal superstructure of DBA⊂R-Δ.
FIG. 10B depicts a single-crystal superstructure of DBA⊂S-Δ. In both FIGS. 10A and 10B, the C, tan; H, white; O, red; N, blue; Br, brown; and the purple dash lines indicate [Br . . . Br] and [Br . . . π] interactions.
Figure 11:
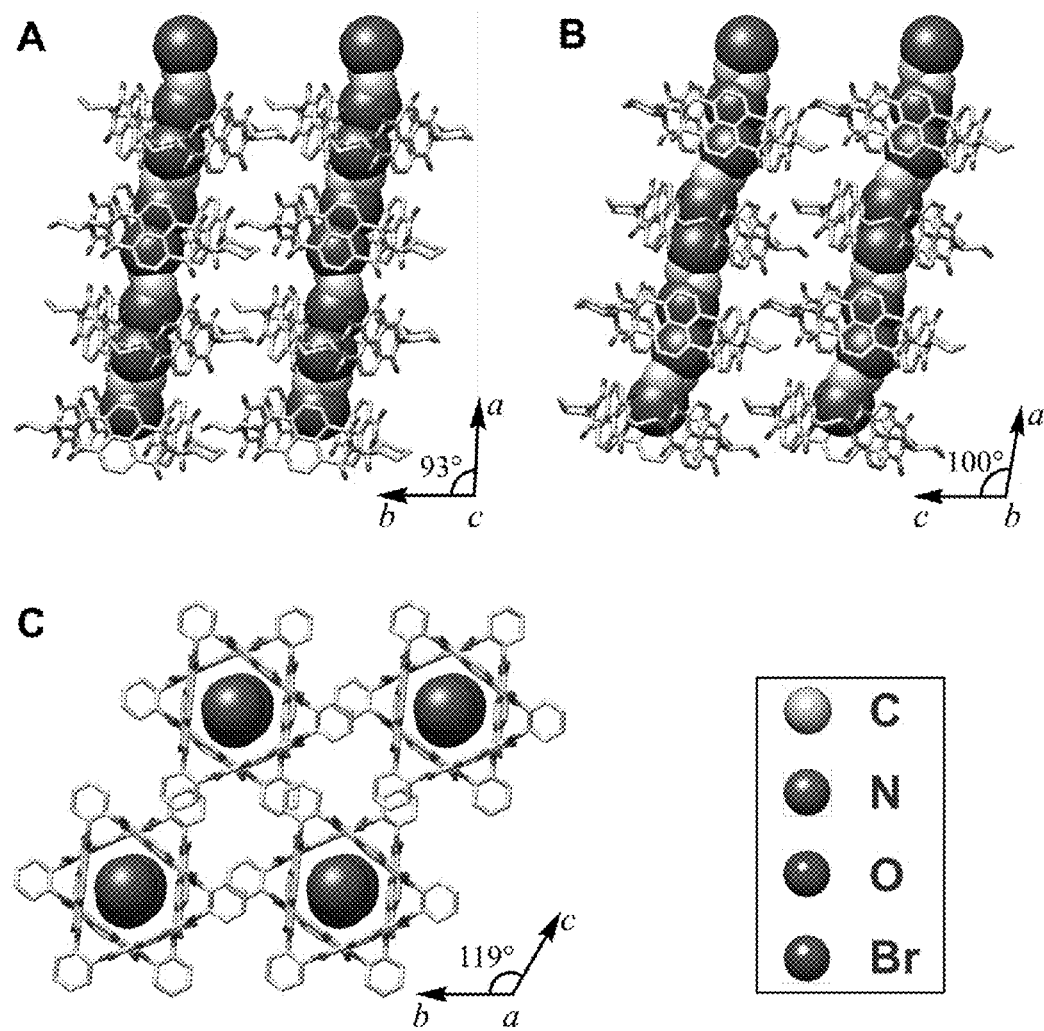
FIG. 11A depicts front and side views show the parallel arrangement of the 1D superstructure of DBA⊂R-Δ.
FIG. 11B depicts front and side views show the parallel arrangement of the 1D superstructures of DBA⊂R-Δ.
FIG. 11C depicts a top view showing the rhombic arrangement of crystal packing for DBA⊂R-Δ, wherein atom colors are as follows for FIGS. 11A, 11B and 11C: C, tan; O, red; N, blue; Br, brown. Hydrogen atoms have been omitted for the sake of clarity.
Figure 12:
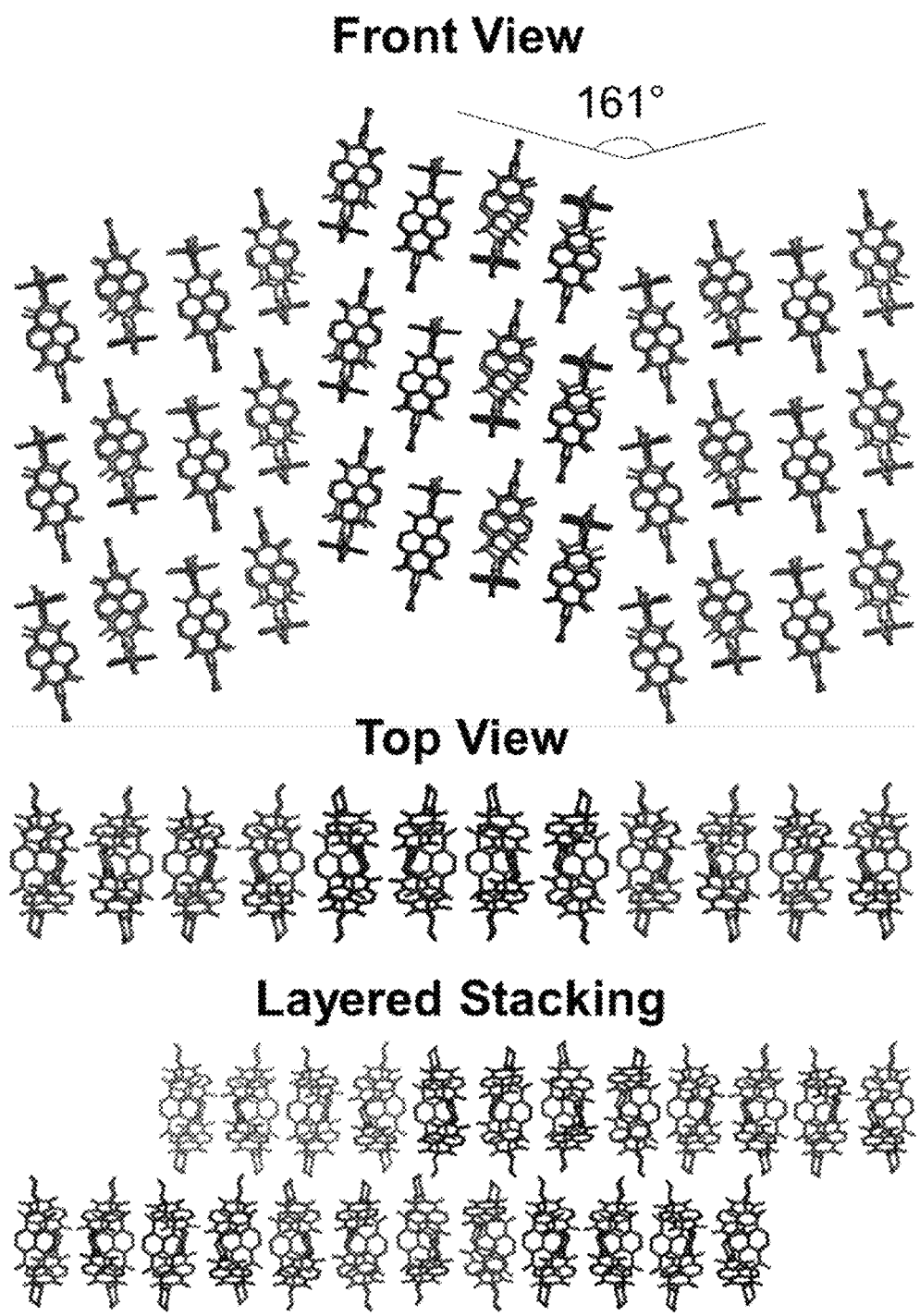
FIG. 12 depicts the zigzag arrangement with an angle of 161° of the tetramers of complex DCA⊂R-Δ (denoted as "front view"). In the perspective denoted as "top view," the 2D layer superstructures are shown either unstacked or stacked with some offset between layers. Two different orientations of tetrameric helical tubes were depicted with red and blue colors, respectively.

SADABS-2008/1 (Bruker, 2008) was used for absorption correction. The structure was solved by direct methods and refined subsequently using the Bruker SHELXTL software package. The majority of the hydrogen atoms were assigned riding isotropic displacement parameters and constrained to idealized geometries. Crystallographic images were produced using UCSF Chimera 1.8.1. Atom-to-atom distances and angles were measured employing Mercury 3.3. FIG. 10 shows the single-crystal superstructures of DBA ⊂ R-Δ and DBA ⊂ S-Δ. FIGS. 11 and 12 illustrate the crystal packing of DBA ⊂ R-Δ and DCA ⊂ R-Δ, respectively. Table 2 reports the [C—H . . . O] hydrogen bonding geometries of DBA ⊂ R-Δ and DCA ⊂ R-Δ. CCDC 1019481-1019484 contain the supplementary crystallographic data. These data can be obtained free of charge from the Cambridge Crystallographic Data Centre.

TABLE 2

[C—H . . . O] Hydrogen bonding geometries of DBA ⊂ R-Δ and DCA ⊂ R-Δ

| Complex | H-Bonded R-Δ Dimer | [C—H . . . O] | $d_{C—H}$/Å | $d_{C—H . . . O}$/Å | $d_{C . . . O}$/Å | ∠C—H . . . O/° |
|---|---|---|---|---|---|---|
| DBA ⊂ R-Δ | a & b | C50—H50 . . . O19 | 0.950 | 2.58(1) | 3.43(2) | 150(1) |
|  |  | C89—H89 . . . O12 | 0.950 | 2.19(1) | 3.10(2) | 160(1) |
|  |  | C30—H30 . . . O15 | 0.950 | 2.21(1) | 3.14(2) | 164(1) |
|  |  | C69—H69 . . . O8 | 0.950 | 2.45(1) | 3.28(2) | 146(1) |
|  |  | C10—H10 . . . O23 | 0.950 | 2.71(2) | 3.66(2) | 175(1) |
|  |  | C108—H108 . . . O4 | 0.950 | 2.39(1) | 3.34(2) | 178(1) |
|  | b & a | C102—H102 . . . O10 | 0.950 | 2.46(1) | 3.37(2) | 159(1) |
|  |  | C44—H44 . . . O21 | 0.950 | 2.515(9) | 3.44(2) | 164(1) |
|  |  | C83—H83 . . . O6 | 0.950 | 2.44(1) | 3.30(2) | 152(1) |
|  |  | C24—H24 . . . O17 | 0.950 | 2.31(1) | 3.23(2) | 161(1) |
|  |  | C63—H63 . . . O2 | 0.950 | 2.32(1) | 3.23(2) | 161(1) |
|  |  | C4—H4 . . . O13 | 0.950 | 2.48(2) | 3.28(3) | 141(1) |
| DCA ⊂ R-Δ | a & b | C36—H0AA . . . O2A | 0.950 | 2.351(5) | 3.26(1) | 159.4(7) |
|  |  | C10A—H0DA . . . O8 | 0.950 | 2.369(6) | 3.29(1) | 162.4(5) |
|  |  | C16—HM . . . O10A | 0.950 | 2.356(5) | 3.19(1) | 146.0(5) |
|  |  | C50A—H8FA . . . O4 | 0.948 | 2.464(5) | 3.343(9) | 154.1(5) |
|  |  | C56—H4BA . . . O6A | 0.951 | 2.344(6) | 3.26(1) | 161.4(5) |
|  |  | C30A—H4EA . . . O12 | 0.951 | 2.486(6) | 3.37(1) | 154.8(5) |
|  | b & a' | C16A—H2DA . . . O4B | 0.948 | 2.340(6) | 3.28(1) | 169.8(5) |
|  |  | C16B—H4HA . . . O4A | 0.950 | 2.283(6) | 3.23(1) | 173.9(5) |
|  |  | C56A—H0GA . . . O8B | 0.951 | 2.501(6) | 3.32(1) | 144.6(5) |
|  |  | C36B—H8IA . . . O12A | 0.949 | 2.277(5) | 3.197(9) | 163.2(5) |
|  |  | C36A—H6EA . . . O12B | 0.951 | 2.363(6) | 3.15(1) | 140.6(6) |
|  |  | C56B—H2KA . . . O8A | 0.949 | 2.584(6) | 3.28(1) | 130.1(6) |
|  | a' & b' | C50B—H0KA . . . O12C | 0.949 | 2.281(6) | 3.23(1) | 176.1(6) |
|  |  | C56C—H56C . . . O10B | 0.950 | 2.268(6) | 3.18(1) | 159.5(5) |
|  |  | C10B—H2HA . . . O4C | 0.951 | 2.269(5) | 3.18(1) | 159.5(5) |
|  |  | C16C—H16C . . . O2B | 0.950 | 2.305(6) | 3.222(9) | 162.0(5) |
|  |  | C30B—H6IA . . . O8C | 0.950 | 2.408(7) | 3.26(1) | 148.8(5) |
|  |  | C36C—H36C . . . O6B | 0.948 | 2.252(6) | 3.18(1) | 166.4(6) |

Example 5

Cyclic Voltammetry

Cyclic voltammetry (CV) was carried out in $CH_2Cl_2$ solutions of the aromatic diimide derivatives using $[Bu_4N][PF_6]$ as the supporting electrolyte. The CVs for pyromellitic and naphthalene diimides are characterized by sequential one-electron reduction processes. The CV of pyromellitic diimide (PMI-Ref) shows a first reduction potential at −1131 mV, corresponding to the formation of the $[PMI]^{·-}$ radical anion. The redox potential corresponding to the generation of the $[PMI]^{2-}$ dianion is too close to that of the solvent and so does not permit an accurate determination of the second redox potential. The CV of (+)-PMI-Δ reveals a splitting of the redox wave into three distinct reversible one-electron reductions. The first redox potential related to the generation of $[(+)-PMI-Δ]^{·-}$ mono radical anion is shifted towards less negative potentials by 108 mV, compared to the formation of the $[PMI-Ref]^{·-}$ radical anion, as a consequence of the electronic communication between the PMI units of (+)-PMI-Δ. Similar, but more pronounced electron sharing effects are observed in the case of the NDI-prism (−)-NDI-Δ (FIG. 2).

The reduction potential of the reference pyromellitic and naphthalene diimides are in agreement with previously reported values for similar compounds. The first one-electron reduction process, $E_1$, and a second two-electron process, $E_2$, for the pyromellitic and naphthalene diimide derivatives investigated in this study are summarized in Table 3.

TABLE 3

Summary of the average redox potentials ($E_{1/2}$ vs. Ag/AgCl) of (−)-NDI-Δ and (+)-PMI-Δ along with those for the reference compounds NDI-Ref and PMI-Ref with cyclohexyl substituents.[a]

| R | $E_1$/mV | | $E_2$/mV | |
|---|---|---|---|---|
| | Δ | Ref | Δ | Ref |
| 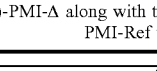 | −567 ± 7<br>−704 ± 5<br>−813 ± 9 | −709 ± 5 | −1255 ± 6<br>−1374 ± 8<br>−1506 ± 9 | −1131 ± 9 |
|  | −807 ± 5<br>−928 ± 8<br>−1040 ± 7 | −915 ± 6 | N.A. | N.A. |

[a]Average potentials were determined after three runs by cyclic voltammetry in $CH_2Cl_2$ at a concentration of 0.5 mM with a scan rate of 50 mVs$^{-1}$. Error bars represent standard deviations.

Example 6

Spectroelectrochemistry and UV/Vis Titration with $CoCp_2$

Spectroelectrochemistry was performed on $CH_2Cl_2$ solutions (60 μM) of (−)-NDI-Δ in order to shed more light on the optical properties associated with the electrochemical redox processes. On setting the voltage (vs. Ag/AgCl) of the working electrode at −650 mV, the distinctive absorption bands of $NDI^{·-}$ radical anion can be observed. The conversion to the diradical dianionic state $[(-)-NDI-Δ]^{2(·-)}$ and trisradical trianionic state $[(-)-NDI-Δ]^{3(·-)}$ was achieved by applying potentials of −800 and −1100 mV, respectively. The shift of the applied potential to more negative values results in an increase of the characteristic absorption bands of the $[NDI]^{·-}$ and in a gradual blue-shift of the long wavelength (X>700 nm) adsorption, which is related to the $D_0 \rightarrow D_1$ transition. The observed changes in the maximum absorption for the different oxidation states can be attributed to the electron sharing in the mono-radical anion form of (−)-NDI-Δ. The fact that the radical anionic states of the NDI-prism (−)-NDI-Δ are reversible is demonstrated by the restoration of the original spectrum of (−)-NDI-Δ after re-oxidation by holding the potential at 0 V for 30 min.

The UV/Vis spectra for the reduced states of (−)-NDI-Δ, obtained by spectroelectrochemical methods, were confirmed with stepwise chemical reduction of (−)-NDI-Δ with the one-electron reductant cobaltocene ($CoCp_2$). The spectroscopic titration (Figure S7) of CoCp2 into a 10 μM solution of (−)-NDI-Δ in $CH_2Cl_2$ was carried out in a glovebox under an Argon atmosphere. The addition of the reductant produces highly featured adsorption spectra, which display the characteristic peaks of $[NDI]^{·-}$. The long wavelength adsorption peaks for the mono-radical anion $[(-)-NDI-Δ]^{(·-)}$ display the same shifts as observed in the UV-Vis spectroelectrochemical experiments. The UV-Vis spectrum of the NDI-prism (−)-NDI-Δ, upon the addition of 1.0 equiv of the reductant, can be compared with the spectra for the reference compound NDI-Ref. A red-shift in the adsorption peaks at longer wavelength was observed for spectra of (−)-NDI-Δ, in keeping with the hypothesis that electron sharing among the NDI-units is taking place in the $[(-)-NDI-Δ]^{(·-)}$ radical anion.

Example 7

Quantum Mechanical Calculations

Density Functional Theory (DFT) calculations were performed using the Jaguar software package. The pseudospectral methodology, which significantly speeds up the SCF iterations, was employed in all calculations. Default grids and SCF convergence criteria, as implemented in Jaguar, were used. Structures of (−)- and (+)-NDI-Δ, (−)-PMI-Δ, NDI-Ref, and PMI-Ref were optimized at the B3LYP/6-31G level of theory in their neutral and mono-radical anionic forms. The complex of (+)-NDI-Δ with $I_3$ was optimized at the B3LYP-D3/LACVP level of theory.

Redox Potentials. Standard free energies of reduction were computed by subtracting the energies (B3LYP/6-311++G//B3LYP/6-31G level) of the oxidized from the energies of the corresponding reduced species in vacuum. Solvation contributions, estimated with single-point calculations at the B3LYP/6-31G** level, using the implicit Poisson-Boltzman solvation model implemented in Jaguar, were then added to the vacuum energies. Conversion of the free energies to redox potentials was achieved using standard formulas and the standard reduction potential for the normal hydrogen electrode (NHE) set to 4.28 V.

Interaction Energies. Counterpoise corrected interaction energies of a π-stacked NDI-Δ dimer (FIG. 4A) with and without bound $[Bu_4N][I_3]$ were calculated at the M06-2X/LACVP** level. Coordinates were taken from the single crystal X-ray structure of $[Bu_4N][I_3 \subset (+)-NDI-Δ]$.

REFERENCES

Schneebeli S T, Frasconi M, Liu Z, Wu Y, Gardner D M, Strutt N L, Cheng C, Carmieli R, Wasielewski M R, Stoddart J F, "Electron Sharing and Anion-π Recognition in Molecular Triangular Prisms," Angew. Chem. Int. Ed. Engl. 52:13100-4 (2013).

Liu Z, Liu G, Wu Y, Cao D, Sun J, Schneebeli S T, Nassar M S, Mirkin C A, Stoddart J F, "Assembly of supramolecular nanotubes from molecular triangles and 1,2-dihalohydrocarbons," J. Am. Chem. Soc. 136:16651-60 (2014).

All of the patents, patent applications, patent application publications, other publications and citations of data publicly available in government-, academic- or industry-supported data bases recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. A redox-active triangular prism, comprising:
a plurality of pure enantiomers selected from a group consisting of the following:

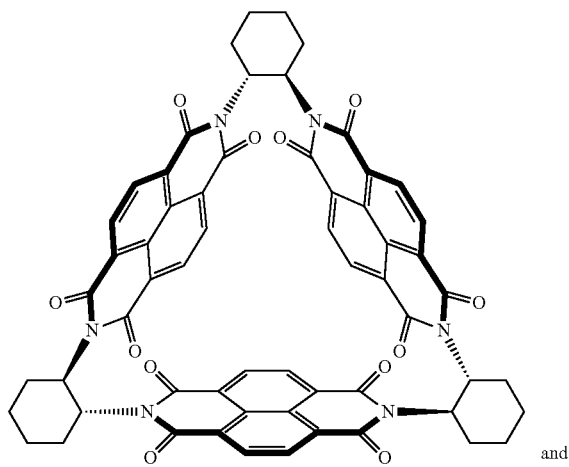

(−)-NDI-Δ and

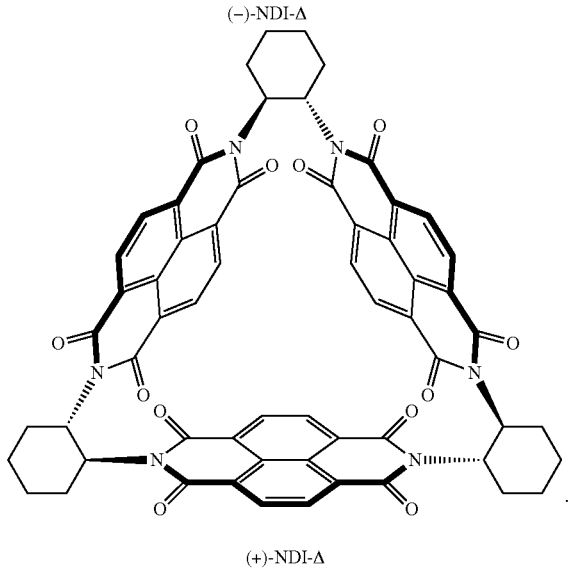

(+)-NDI-Δ

2. The redox-active triangular prism of claim 1, wherein the plurality of pure enantiomers form a structure having a central cavity.

3. The redox-active triangular prism of claim 1, wherein the central cavity comprises sufficient dimensions to accommodate a guest anion.

4. The redox-active triangular prism of claim 1, wherein structure is stabilized through π-π interactions among adjacent members of the plurality of pure enantiomers upon binding a guest anion.

5. The redox-active triangular prism of claim 1, wherein the structure comprises a redox activity of greater than two reversible one-electron cathodic waves.

6. The redox-active triangular prism of claim 1, wherein the plurality of pure enantiomers consist of (−)-NDI-Δ.

7. The redox-active triangular prism of claim of claim 6, wherein the plurality of pure enantiomers form a structure having a central cavity, wherein the structure is selected from a group consisting of a right-handed, supramolecular (P)-helix, an organogel, a non-helical supramolecular nanotube and a (P)-helical supramolecular nanotube.

8. The redox-active triangular prism of claim of claim 6, wherein the structure is an organogel comprising a plurality of intertwining supramolecular nanotubes.

9. The redox-active triangular prism of claim 1, wherein the plurality of pure enantiomers consist of (+)-NDI-Δ.

10. The redox-active triangular prism of claim 9, wherein the plurality of pure enantiomers form a structure having a central cavity, wherein the structure is selected from a group consisting of a left-handed, supramolecular (M)-helix and a (M)-helical supramolecular nanotube.

11. A method of making a redox-active triangular prism, comprising:
preparing a mixture comprising naphthalene-tetracarboxylic dianhydride, a pure enantiomer selected from a group consisting of (RR)-trans-1,2-cyclohexanediamine and (SS)-trans-1,2-cyclohexanediamine and a solvent; and
incubating the mixture at a temperature above ambient temperature, wherein the redox-active triangular prism formed is a member selected from a group consisting of the following:

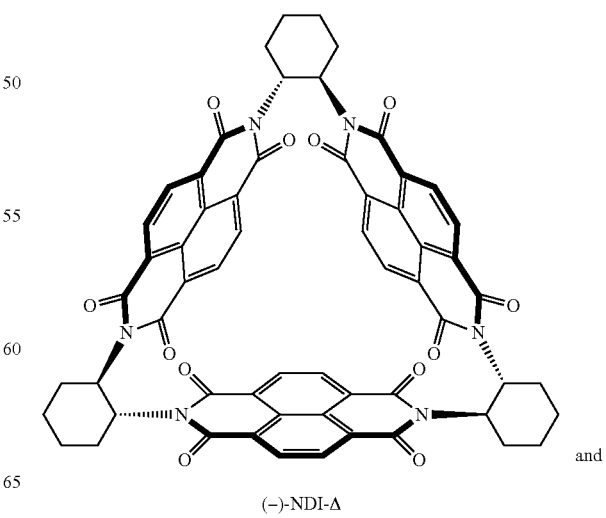

(−)-NDI-Δ and

-continued

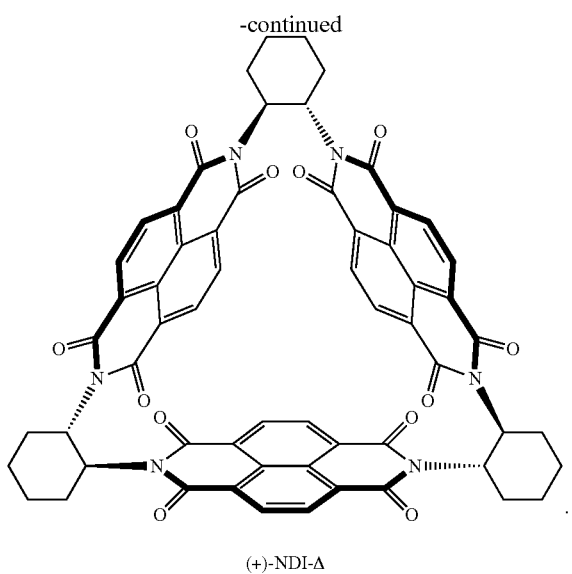

(+)-NDI-Δ

12. The method of claim 11, wherein the solvent comprises an organic solvent.

13. The method of claim 12, wherein the organic solvent comprises dimethylformamide.

14. The method of claim 11, wherein the pure enantiomer consists of (RR)-trans-1,2-cyclohexanediamine and the redox-active triangular prism formed is the following:

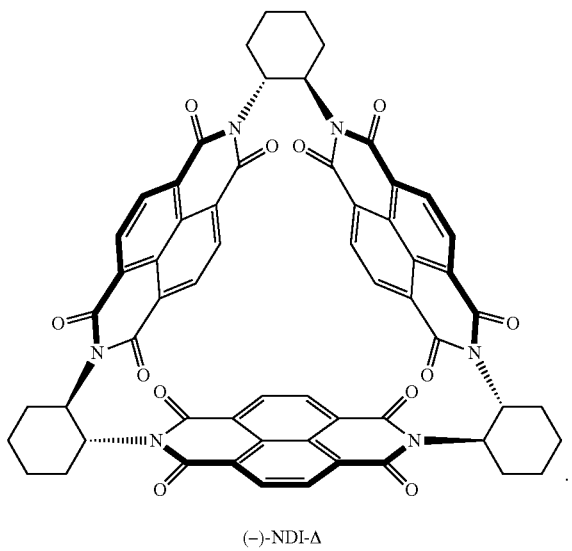

(−)-NDI-Δ

15. The method of claim 14, further comprising:
purifying (−)-NDI-Δ product by chromatography; and
precipitating (−)-NDI-Δ.

16. The method of claim 15, further comprising:
preparing a solution comprising (−)-NDI-Δ and a solvent; and
diffusing n-hexane in the solution to form complexes comprising solvent and (−)-NDI-Δ.

17. The method of claim 16, wherein the solvent is selected from a group consisting of (E)-1,2-dichloroethene, BrCH$_2$CH$_2$Br, ClCH$_2$CH$_2$Br, ClCH$_2$CH$_2$I and ClCH$_2$CH$_2$Cl.

18. The method of claim 11, wherein the pure enantiomer consists of (SS)-trans-1,2-cyclohexanediamine and the redox-active triangular prism formed is the following:

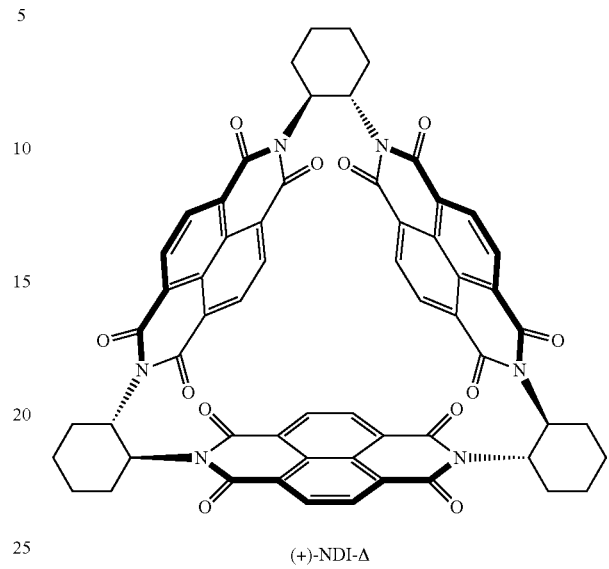

(+)-NDI-Δ

19. The method of claim 18, further comprising:
purifying (+)-NDI-Δ product chromatography over silica gel; and
precipitating (+)-NDI-Δ.

20. The method of claim 19, further comprising:
preparing a solution comprising (+)-NDI-Δ and solvent; and
diffusing n-hexane in the solution to form complexes comprising solvent and (+)-NDI-Δ.

21. The method of claim 20, wherein the solvent is selected from a group consisting of (E)-1,2-dichloroethene, BrCH$_2$CH$_2$Br, ClCH$_2$CH$_2$Br, ClCH$_2$CH$_2$I and ClCH$_2$CH$_2$Cl.

22. An electrode comprising a redox-active triangular prism, wherein the redox-active triangular prism comprises:
a plurality of pure enantiomers selected from a group consisting of the following:

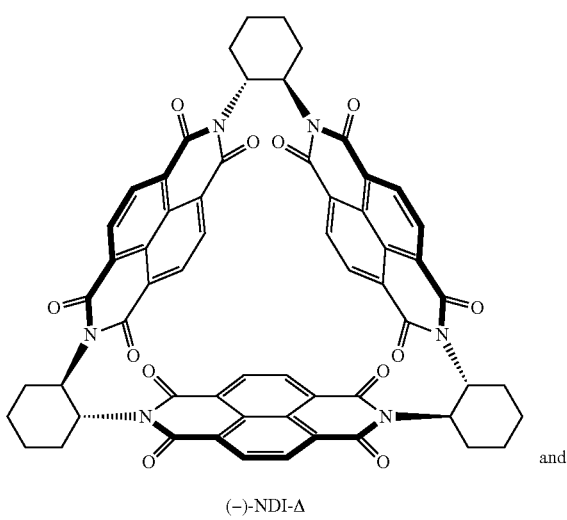

(−)-NDI-Δ and

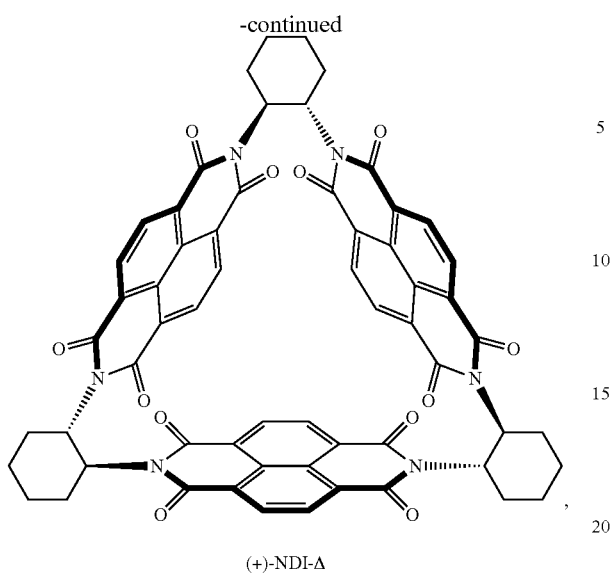
(+)-NDI-Δ
or a solvent-crystalline complex thereof.
* * * * *